United States Patent
Chang et al.

(10) Patent No.: US 10,053,737 B2
(45) Date of Patent: Aug. 21, 2018

(54) METHODS AND COMPOSITIONS FOR TREATING CANCER BY IDENTIFYING ONE OR MORE ERK MUTATIONS

(71) Applicant: Merck Sharp & Dohme Corp., Rahway, NJ (US)

(72) Inventors: Ken C. N. Chang, Yardley, PA (US); Stefan Galuska, North Plainfield, NJ (US); Matthew J. Marton, Whitehouse Station, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 385 days.

(21) Appl. No.: 14/781,952

(22) PCT Filed: Apr. 3, 2014

(86) PCT No.: PCT/US2014/032745
§ 371 (c)(1),
(2) Date: Oct. 2, 2015

(87) PCT Pub. No.: WO2014/168801
PCT Pub. Date: Oct. 16, 2014

(65) Prior Publication Data
US 2016/0040252 A1    Feb. 11, 2016

Related U.S. Application Data

(60) Provisional application No. 61/809,612, filed on Apr. 8, 2013.

(51) Int. Cl.
| | | |
|---|---|---|
| C12P 19/34 | (2006.01) |
| C12Q 1/6886 | (2018.01) |
| A61K 31/416 | (2006.01) |
| C12Q 1/6858 | (2018.01) |

(52) U.S. Cl.
CPC .......... *C12Q 1/6886* (2013.01); *A61K 31/416* (2013.01); *C12Q 1/6858* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2010/0248252 A1 | 9/2010 | Shuber et al. | |
| 2010/0286143 A1* | 11/2010 | Dias-Santagata | C12Q 1/6858 514/234.5 |
| 2011/0129832 A1 | 6/2011 | Makarov et al. | |
| 2011/0158944 A1 | 6/2011 | Hosted et al. | |

FOREIGN PATENT DOCUMENTS

| | | |
|---|---|---|
| WO | 2003071252 A2 | 8/2003 |
| WO | 2012028746 A1 | 3/2012 |
| WO | 2012049279 A1 | 4/2012 |
| WO | 2012129352 A1 | 9/2012 |
| WO | 2014168801 A2 | 10/2014 |

OTHER PUBLICATIONS

Chang KCN et al., Development and validation of a clinical trial patient stratification assay that interrogates 27 mutation sites in MAPK pathway genes, Plos One, Aug. 2013, pp. 1-17, 8(8).
Supplementary European Search Report, PCT/US2014/032745, 14783222.4-1403, dated Dec. 23, 2016, 10 pages.

* cited by examiner

*Primary Examiner* — Kenneth R Horlick
(74) *Attorney, Agent, or Firm* — Richard S. Parr; Catherine D. Fitch

(57) ABSTRACT

The invention is directed to methods, reagents, and kits for the detection of MAPK/ERK pathway mutations in a patient diagnosed for cancer. In one embodiment, the invention comprises a sensitive and selective method to identify mutations to the BRAF, KRAS, and NRAS genes in a single reaction. In another aspect of this embodiment, the invention comprises primers and probes for the detection of the BRAF, KRAS, and NRAS mutations using a single nucleotide primer extension assay. In another embodiment the invention is used to identify and select patients amenable for treatment with an ERK inhibitor.

15 Claims, 10 Drawing Sheets

BRAF EXON 11

GTGATGATTGGAGAGATTCCTGATGGGCAGATTACAGTGGGACACAAAGAATTGGATCTCATTTGGAAC
AGTCTACAAGGGAAAGTGGCAGTGATGTGGCAGTGAAAATGTTGAATGTGACAGCACCTACACCTCAG
(SEQ ID NO: 101)

BRAF EXON 15

ATGGATTACTTACACGGCCAAGTCAATCATCCACAGAGACCTCAAGAGTAATAATATATTTCTTCATGAAG
ACCTCACAGTAAAAATAGGTGATTTTGGTCTAGCTACAGTGAAATCTCGATGGAGTGGGTCCCATCAGTT
TGAACAGTTGTCTGGATCCATTTTGTGAATGGCACCAGAAGTCATCAGAATGCAAGATAAAAATCCATAC
(SEQ ID NO: 102)

FIG.6A

NRAS EXON 2

TTACTGGTTTCCAACAGGTTCTTGCTGGTGTGAAATGACTGAGTACAAACTGGTGGTTGGAGCAGGT
GGTGTTGGGAAAGCGCACTGACAATCCAGCTAATCCAGAACCACTTTGTAGATGAATATGATCCACCA
TAGAGGTGAGGCCCAGTGGTAGCCCGCTGACCCTGTCTCTCCACTTGTCGGATCCATCTTTACCCAT
(SEQ ID NO: 103)

NRAS EXON 3

ATAGATGGTGAAACCTGTTTGTTGGACATACTGGATACAGCTGGACAAGAAGAGTACAGTGCCATGAGAG
ACCAATACATGAGGACAGCGAAGGCTTCCTCTGTGTATTGCCATCAATAATAGCAAGTCATTTGCGGA
(SEQ ID NO: 104)

FIG.6B

KRAS Exon 2
TAGTGTATTAACCTTATGTGTGACATGTTCTAATATAGTCACATTTCATTATTTTATTATAAGGCCTG
CTGAAAATGACTGAATATAAACTTGTGGTAGTTGGAGCTGGTGGCGTAGGCAAGAGTGCCTTGACGATAC
AGCTAATTCAGAATCATTTGTGACGAATATGATCCAACAATAGAGGTAAATCTTGTTTAATATGCAT
ATTACTGGTGCAGGACCATTCTTTGATACAGATAAAGGTTTCTCTGACCATTTTCATGAGTACTTATTAC
(SEQ ID NO: 105)

KRAS Exon 3
CCTTTTTGAAGTAAAAGGTGCACTGTAATAATCCAGACTGTGTTTCTCCCTTCTCAGGATTCCTACAGG
AAGCAAGTAGTAATTGATGGAGAAACCTGTCTCTTGGATATTCTCGACACAGCAGGTCAAGAGGAGTACA
GTGCAATGAGGGACCAGTACATGAGGACTGGGGAGGGCTTTCTTGTATTGCCATAAATAATACTAA
ATCATTTGAAGATATATTCACCATTATAGGTGGGTTTAAATTGAATATAATAAGCTGACATTAAGGAGTAAT
(SEQ ID NO: 106)

KRAS Exon 4
GAAATAAATGTGATTTGCCTTCTAGAACAGTAGACACAAAACAGGCTCAGGACTTAGCAAGAAGTTATGG
AATTCCTTTTATTGAAACATCAGCAAAAGACAAGACAGGTAGTAACACTGAAATAAATACAGATCTGTTT
TCTGCAAAATCATAACTGTTATGTTCATTTAATATATCAGT
(SEQ ID NO: 107)

FIG.6C

SEQUENCE LISTING

<160> NUMBER OF SEQ ID NOS: 107

<210> SEQ ID NO 1
<211> LENGTH: 27
<212> TYPE: DNA
<213> ORGANISM: Artificial Sequence
<220> FEATURE:
<223> OTHER INFORMATION: PCR PRIMER

<400> SEQUENCE: 1
tgtgacatgt tctaatatag tcacatt         27

<210> SEQ ID NO 2
<211> LENGTH: 23
<212> TYPE: DNA
<213> ORGANISM: Artificial Sequence
<220> FEATURE:
<223> OTHER INFORMATION: PCR PRIMER

<400> SEQUENCE: 2
cacaaaatga ttctgaatta gct         23

<210> SEQ ID NO 3
<211> LENGTH: 22
<212> TYPE: DNA
<213> ORGANISM: Artificial Sequence
<220> FEATURE:
<223> OTHER INFORMATION: PCR PRIMER

<400> SEQUENCE: 3
ggaagcaagt agtaattgat gg         22

<210> SEQ ID NO 4
<211> LENGTH: 16
<212> TYPE: DNA
<213> ORGANISM: Artificial Sequence
<220> FEATURE:
<223> OTHER INFORMATION: PCR PRIMER

<400> SEQUENCE: 4
aaagaaagcc ctcccc         16

<210> SEQ ID NO 5
<211> LENGTH: 22
<212> TYPE: DNA
<213> ORGANISM: Artificial Sequence
<220> FEATURE:
<223> OTHER INFORMATION: PCR PRIMER

<400> SEQUENCE: 5
gaacagtaga cacaaaacag gc         22

<210> SEQ ID NO 6
<211> LENGTH: 26
<212> TYPE: DNA
<213> ORGANISM: Artificial Sequence
<220> FEATURE:
<223> OTHER INFORMATION: PCR PRIMER

<400> SEQUENCE: 6
tgcagaaaac agatctgtat ttattt         26

<210> SEQ ID NO 7
<211> LENGTH: 20
<212> TYPE: DNA
<213> ORGANISM: Artificial Sequence

<220> FEATURE:
<223> OTHER INFORMATION: PCR PRIMER

<400> SEQUENCE: 7
ggtgtgaaat gactgagtac                                               20

<210> SEQ ID NO 8
<211> LENGTH: 19
<212> TYPE: DNA
<213> ORGANISM: Artificial Sequence
<220> FEATURE:
<223> OTHER INFORMATION: PCR PRIMER

<400> SEQUENCE: 8
gggcctcacc tctatggtg                                                19

<210> SEQ ID NO 9
<211> LENGTH: 20
<212> TYPE: DNA
<213> ORGANISM: Artificial Sequence
<220> FEATURE:
<223> OTHER INFORMATION: PCR PRIMER

<400> SEQUENCE: 9
ggtgaaacct gtttgttgga                                               20

<210> SEQ ID NO 10
<211> LENGTH: 20
<212> TYPE: DNA
<213> ORGANISM: Artificial Sequence
<220> FEATURE:
<223> OTHER INFORMATION: PCR PRIMER

<400> SEQUENCE: 10
atacacagag gaagccttcg                                               20

<210> SEQ ID NO 11
<211> LENGTH: 21
<212> TYPE: DNA
<213> ORGANISM: Artificial Sequence
<220> FEATURE:
<223> OTHER INFORMATION: PCR PRIMER

<400> SEQUENCE: 11
tcttcatgaa gacctcacag t                                             21

<210> SEQ ID NO 12
<211> LENGTH: 21
<212> TYPE: DNA
<213> ORGANISM: Artificial Sequence
<220> FEATURE:
<223> OTHER INFORMATION: PCR PRIMER

<400> SEQUENCE: 12
ccagacaact gttcaaactg a                                             21

<210> SEQ ID NO 13
<211> LENGTH: 20
<212> TYPE: DNA
<213> ORGANISM: Artificial Sequence
<220> FEATURE:
<223> OTHER INFORMATION: PCR PRIMER

<400> SEQUENCE: 13
gtgatgattg ggagattcct                                               20

<210> SEQ ID NO 14
<211> LENGTH: 19
<212> TYPE: DNA
<213> ORGANISM: Artificial Sequence
<220> FEATURE:
<223> OTHER INFORMATION: PCR PRIMER

<400> SEQUENCE: 14
ctgccacatc accatgcca                                              19

<210> SEQ ID NO 15
<211> LENGTH: 20
<212> TYPE: DNA
<213> ORGANISM: Artificial Sequence
<220> FEATURE:
<223> OTHER INFORMATION: SNPE PROBE

<400> SEQUENCE: 15
aacttgtggt agttggagct                                             20

<210> SEQ ID NO 16
<211> LENGTH: 26
<212> TYPE: DNA
<213> ORGANISM: Artificial Sequence
<220> FEATURE:
<223> OTHER INFORMATION: SNPE PROBE

<400> SEQUENCE: 16
gatcgtactt gtggtagttg gagctg                                      26

<210> SEQ ID NO 17
<211> LENGTH: 32
<212> TYPE: DNA
<213> ORGANISM: Artificial Sequence
<220> FEATURE:
<223> OTHER INFORMATION: SNPE PROBE

<400> SEQUENCE: 17
gatcgatcga tcttgtggta gttggagctg gt                               32

<210> SEQ ID NO 18
<211> LENGTH: 38
<212> TYPE: DNA
<213> ORGANISM: Artificial Sequence
<220> FEATURE:
<223> OTHER INFORMATION: SNPE PROBE

<400> SEQUENCE: 18
gatcgatcga tcgatcgatg tggtagttgg agctggtg                         38

<210> SEQ ID NO 19
<211> LENGTH: 50
<212> TYPE: DNA
<213> ORGANISM: Artificial Sequence
<220> FEATURE:
<223> OTHER INFORMATION: SNPE PROBE

<400> SEQUENCE: 19
tttttttttt tttttttttt ttttttttct cattgcactg tactcctctt            50

<210> SEQ ID NO 20
<211> LENGTH: 54
<212> TYPE: DNA
<213> ORGANISM: Artificial Sequence
<220> FEATURE:
<223> OTHER INFORMATION: SNPE PROBE -continued

<400> SEQUENCE: 20
tttttttttt tttttttttt tttttttttt ttttattct cgacacagca ggtc    54

<210> SEQ ID NO 21
<211> LENGTH: 63
<212> TYPE: DNA
<213> ORGANISM: Artificial Sequence
<220> FEATURE:
<223> OTHER INFORMATION: SNPE PROBE

<400> SEQUENCE: 21
tttttttttt tttttttttt tttttttttt tttttttttt ttcctcattg cactgtactc    60
ctc    63

<210> SEQ ID NO 22
<211> LENGTH: 74
<212> TYPE: DNA
<213> ORGANISM: Artificial Sequence
<220> FEATURE:
<223> OTHER INFORMATION: SNPE PROBE

<400> SEQUENCE: 22
tttttttttt tttttttttt tttttttttt tttttttttt tttttttttg tcttacttag    60
ctgtcttgtc tttg    74

<210> SEQ ID NO 23
<211> LENGTH: 80
<212> TYPE: DNA
<213> ORGANISM: Artificial Sequence
<220> FEATURE:
<223> OTHER INFORMATION: SNPE PROBE

<400> SEQUENCE: 23
tttttttttt cccccccccc tttttttttt tttttttttt tttttttttt tttttgaat    60 tcctttatt gaaacatcag    80

<210> SEQ ID NO 24
<211> LENGTH: 41
<212> TYPE: DNA
<213> ORGANISM: Artificial Sequence
<220> FEATURE:
<223> OTHER INFORMATION: SNPE PROBE

<400> SEQUENCE: 24
tttttttttt tttttttttt ttctggtggt ggttggagca g    41

<210> SEQ ID NO 25
<211> LENGTH: 47
<212> TYPE: DNA
<213> ORGANISM: Artificial Sequence
<220> FEATURE:
<223> OTHER INFORMATION: SNPE PROBE

<400> SEQUENCE: 25
tttttttttt tttttttttt tttttttgg tggtggttgg agcaggt    47

<210> SEQ ID NO 26
<211> LENGTH: 53
<212> TYPE: DNA
<213> ORGANISM: Artificial Sequence
<220> FEATURE:
<223> OTHER INFORMATION: SNPE PROBE

<400> SEQUENCE: 26
tttttttttt tttttttttt tttttttttt ttgtcagtgc gcttttccca aca    53

<210> SEQ ID NO 27
<211> LENGTH: 59
<212> TYPE: DNA
<213> ORGANISM: Artificial Sequence
<220> FEATURE:
<223> OTHER INFORMATION: SNPE PROBE

<400> SEQUENCE: 27
tttttttttt tttttttttt tttttttttt ttttttctc atggcactgt actcttctt    59

<210> SEQ ID NO 28
<211> LENGTH: 65
<212> TYPE: DNA
<213> ORGANISM: Artificial Sequence
<220> FEATURE:
<223> OTHER INFORMATION: SNPE PROBE

<400> SEQUENCE: 28
tttttttttt tttttttttt tttttttttt tttttttttt tttgacatac tggatacagc    60
tggac    65

<210> SEQ ID NO 29
<211> LENGTH: 71
<212> TYPE: DNA
<213> ORGANISM: Artificial Sequence
<220> FEATURE:
<223> OTHER INFORMATION: SNPE PROBE

<400> SEQUENCE: 29
tttttttttt tttttttttt tttttttttt tttttttttt ttttttttc tctcatggca    60 ctgtactctt c    71

<210> SEQ ID NO 30
<211> LENGTH: 36
<212> TYPE: DNA
<213> ORGANISM: Artificial Sequence
<220> FEATURE:
<223> OTHER INFORMATION: SNPE PROBE

<400> SEQUENCE: 30
tttttttttt ttttcatga agacctcaca gtaaaa    36

<210> SEQ ID NO 31
<211> LENGTH: 42
<212> TYPE: DNA
<213> ORGANISM: Artificial Sequence
<220> FEATURE:
<223> OTHER INFORMATION: SNPE PROBE

<400> SEQUENCE: 31
tttttttttt tttttttttt tacctcacag taaaaatagg tg    42

<210> SEQ ID NO 32
<211> LENGTH: 48
<212> TYPE: DNA
<213> ORGANISM: Artificial Sequence
<220> FEATURE:
<223> OTHER INFORMATION: SNPE PROBE

<400> SEQUENCE: 32
tttttttttt tttttttttt tttttgattt cactgtagct agaccaaa    48

<210> SEQ ID NO 33
<211> LENGTH: 54
<212> TYPE: DNA
<213> ORGANISM: Artificial Sequence
<220> FEATURE:
<223> OTHER INFORMATION: SNPE PROBE

<400> SEQUENCE: 33
tttttttttt tttttttttt tttttttttt tttgagattt cactgtagct agac        54

<210> SEQ ID NO 34
<211> LENGTH: 60
<212> TYPE: DNA
<213> ORGANISM: Artificial Sequence
<220> FEATURE:
<223> OTHER INFORMATION: SNPE PROBE

<400> SEQUENCE: 34
tttttttttt tttttttttt tttttttttt ttttttttttg taaaaatagg tgattttggt    60

<210> SEQ ID NO 35
<211> LENGTH: 66
<212> TYPE: DNA
<213> ORGANISM: Artificial Sequence
<220> FEATURE:
<223> OTHER INFORMATION: SNPE PROBE

<400> SEQUENCE: 35
tttttttttt tttttttttt tttttttttt tttttttttt tttttcatcg agatttcact    60
gtagct        66

<210> SEQ ID NO 36
<211> LENGTH: 35
<212> TYPE: DNA
<213> ORGANISM: Artificial Sequence
<220> FEATURE:
<223> OTHER INFORMATION: SNPE PROBE

<400> SEQUENCE: 36
tttttttttt tttggtgatt ttggtctagc tacaa        35

<210> SEQ ID NO 37
<211> LENGTH: 41
<212> TYPE: DNA
<213> ORGANISM: Artificial Sequence
<220> FEATURE:
<223> OTHER INFORMATION: SNPE PROBE

<400> SEQUENCE: 37
tttttttttt tttttttttg gtgatttttgg tctagctaca g        41

<210> SEQ ID NO 38
<211> LENGTH: 47
<212> TYPE: DNA
<213> ORGANISM: Artificial Sequence
<220> FEATURE:
<223> OTHER INFORMATION: SNPE PROBE

<400> SEQUENCE: 38
tttttttttt tttttttttt tttttttggac ccactccatc gagattt        47

<210> SEQ ID NO 39
<211> LENGTH: 53
<212> TYPE: DNA

```
<213> ORGANISM: Artificial Sequence
<220> FEATURE:
<223> OTHER INFORMATION: SNPE PROBE

<400> SEQUENCE: 39
tttttttttt tttttttttt tttttttttt ttggtgattt tggtctagct aca        53

<210> SEQ ID NO 40
<211> LENGTH: 59
<212> TYPE: DNA
<213> ORGANISM: Artificial Sequence
<220> FEATURE:
<223> OTHER INFORMATION: SNPE PROBE

<400> SEQUENCE: 40
tttttttttt tttttttttt tttttttttt tttttttttg gacccactcc atcgagatt  59

<210> SEQ ID NO 41
<211> LENGTH: 65
<212> TYPE: DNA
<213> ORGANISM: Artificial Sequence
<220> FEATURE:
<223> OTHER INFORMATION: SNPE PROBE

<400> SEQUENCE: 41
tttttttttt tttttttttt tttttttttt tttttttttt tttttgggac aaagaattgg 60
atctg                                                             65

<210> SEQ ID NO 42
<211> LENGTH: 71
<212> TYPE: DNA
<213> ORGANISM: Artificial Sequence
<220> FEATURE:
<223> OTHER INFORMATION: SNPE PROBE

<400> SEQUENCE: 42
tttttttttt tttttttttt tttttttttt tttttttttt tttttttttc cttgtagact 60
gttccaaatg a                                                      71

<210> SEQ ID NO 43
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 43
tacagtggga caaagaattg gatctggatc atttggaaca gtctacaagg gaa        53

<210> SEQ ID NO 44
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 44
ttcccttgta gactgttcca aatgatccag atccaattct tgtcccact gta         53

<210> SEQ ID NO 45
<211> LENGTH: 53
<212> TYPE: DNA
<213> ORGANISM: Artificial Sequence
<220> FEATURE:
<223> OTHER INFORMATION: Synthetic Oligonucleotide
```

<400> SEQUENCE: 45
ttcccttgta gactgttcca aatgattcag atccaattct ttgtcccact gta        53

<210> SEQ ID NO 46
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 46
tacagtggga caaagaattg gatctgtatc atttggaaca gtctacaagg gaa        53

<210> SEQ ID NO 47
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 47
tcactgtagc tagaccaaaa tcacctattt ttactgtgag gtcttcatga aga        53

<210> SEQ ID NO 48
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 48
tcactgtagc tagaccaaaa tcacctagtt ttactgtgag gtcttcatga aga        53

<210> SEQ ID NO 49
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 49
tgaagacctc acagtaaaaa taggtgattt tggtctagct acagtgaaat ctc        53

<210> SEQ ID NO 50
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 50
gagatttcac tgtagctaga ccaaaatcac ctattttac tgtgaggtct tca        53

<210> SEQ ID NO 51
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 51
gagatttcac tgtagctaga ccaaaaacac ctatttttac tgtgaggtct tca        53

<210> SEQ ID NO 52

```
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 52
tgaagacctc acagtaaaaa taggtgaatt tggtctagct acagtgaaat ctc          53

<210> SEQ ID NO 53
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 53
tgaagacctc acagtaaaaa taggtgagtt tggtctagct acagtgaaat ctc          53

<210> SEQ ID NO 54
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 54
cctcacagta aaataggtg attttggtct agctacagtg aaatctcgat gga           53

<210> SEQ ID NO 55
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 55
tccatcgaga tttcactgta gctagaccaa atcacctat ttttactgtg agg           53

<210> SEQ ID NO 56
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 56
cctcacagta aaataggtg attttcgtct agctacagtg aaatctcgat gga           53

<210> SEQ ID NO 57
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 57
cctcacagta aaataggtg attttcgttc agctacagtg aaatctcgat gga           53

<210> SEQ ID NO 58
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 58
```
tccatcgaga tttcactgta gctgaacgaa aatcacctat ttttactgtg agg          53

<210> SEQ ID NO 59
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 59
aataggtgat tttggtctag ctacagtgaa atctcgatgg agtgggtccc atc          53

<210> SEQ ID NO 60
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 60
gatgggaccc actccatcga gatttcactg tagctagacc aaaatcacct att          53

<210> SEQ ID NO 61
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 61
gatgggaccc actccatcga gatttctctg tagctagacc aaaatcacct att          53

<210> SEQ ID NO 62
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 62
gatgggaccc actccatcga gatttccttg tagctagacc aaaatcacct att          53

<210> SEQ ID NO 63
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 63
gatgggaccc actccatcga gatttctttg tagctagacc aaaatcacct att          53

<210> SEQ ID NO 64
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 64
aataggtgat tttggtctag ctacagataa atctcgatgg agtgggtccc atc          53

<210> SEQ ID NO 65
<211> LENGTH: 53
<212> TYPE: DNA

<213> ORGANISM: Artificial Sequence
<220> FEATURE:
<223> OTHER INFORMATION: Synthetic Oligonucleotide

<400> SEQUENCE: 65
gatgggaccc actccatcga gatttatctg tagctagacc aaaatcacct att        53

<210> SEQ ID NO 66
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 66
aggtgatttt ggtctagcta cagtggaatc tcgatggagt gggtcccatc agt        53

<210> SEQ ID NO 67
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 67
gtatcgtcaa ggcactcttg cctacgccac cagctccaac taccacaagt tta        53

<210> SEQ ID NO 68
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 68
gtatcgtcaa ggcactcttg cctacgccac tagctccaac taccacaagt tta        53

<210> SEQ ID NO 69
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 69
gtatcgtcaa ggcactcttg cctacgccac aagctccaac taccacaagt tta        53

<210> SEQ ID NO 70
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 70
gtatcgtcaa ggcactcttg cctacgccat cagctccaac taccacaagt tta        53

<210> SEQ ID NO 71
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 71
gtatcgtcaa ggcactcttg cctacgccag cagctccaac taccacaagt tta        53

<210> SEQ ID NO 72
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 72
gtatcgtcaa ggcactcttg cctacgccaa cagctccaac taccacaagt tta    53

<210> SEQ ID NO 73
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 73
gtatcgtcaa ggcactcttg cctacgccac cagctccaac taccacaagt tta    53

<210> SEQ ID NO 74
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 74
gtatcgtcaa ggcactcttg cctacgcgac cagctccaac taccacaagt tta    53

<210> SEQ ID NO 75
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 75
gtatcgtcaa ggcactcttg cctacgtcac cagctccaac taccacaagt tta    53

<210> SEQ ID NO 76
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 76
cttggatatt ctcgacacag caggtcaaga ggagtacagt gcaatgaggg acc    53

<210> SEQ ID NO 77
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 77
ggtccctcat tgcactgtac tcctcttgac ctgctgtgtc gagaatatcc aag    53

<210> SEQ ID NO 78
<211> LENGTH: 53
<212> TYPE: DNA
<213> ORGANISM: Artificial Sequence
<220> FEATURE:

<223> OTHER INFORMATION: Synthetic Oligonucleotide

<400> SEQUENCE: 78
cttggatatt ctcgacacag caggtaaaga ggagtacagt gcaatgaggg acc      53

<210> SEQ ID NO 79
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 79
ggtccctcat tgcactgtac tcctctttac ctgctgtgtc gagaatatcc aag      53

<210> SEQ ID NO 80
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 80
cttggatatt ctcgacacag caggtcacga ggagtacagt gcaatgaggg acc      53

<210> SEQ ID NO 81
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 81
cttggatatt ctcgacacag caggtcatga ggagtacagt gcaatgaggg acc      53

<210> SEQ ID NO 82
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 82
tggaattcct tttattgaaa catcagcaaa gacaagacag gtaagtaaca ctg      53

<210> SEQ ID NO 83
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 83
cagtgttact tacctgtctt gtctttgctg atgtttcaat aaaaggaatt cca      53

<210> SEQ ID NO 84
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 84
cagtgttact tacctgtctt gtctttgttg atgtttcaat aaaaggaatt cca      53

```
<210> SEQ ID NO 85
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 85
tggaattcct tttattgaaa catcaacaaa gacaagacag gtaagtaaca ctg         53

<210> SEQ ID NO 86
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 86
tggaattcct tttattgaaa catcagtaaa gacaagacag gtaagtaaca ctg         53

<210> SEQ ID NO 87
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 87
cagtgttact tacctgtctt gtctttactg atgtttcaat aaaaggaatt cca         53

<210> SEQ ID NO 88
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 88
caaactggtg gtggttggag caggtggtgt tgggaaaagc gcactgacaa tcc         53

<210> SEQ ID NO 89
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 89
ggattgtcag tgcgcttttc ccaacaccac ctgctccaac caccaccagt ttg         53

<210> SEQ ID NO 90
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 90
caaactggtg gtggttggag cagatggtgt tgggaaaagc gcactgacaa tcc         53

<210> SEQ ID NO 91
<211> LENGTH: 53
<212> TYPE: DNA
<213> ORGANISM: Artificial Sequence
<220> FEATURE:
<223> OTHER INFORMATION: Synthetic Oligonucleotide
```

<400> SEQUENCE: 91
caaactggtg gtggttggag cagttggtgt tgggaaaagc gcactgacaa tcc         53

<210> SEQ ID NO 92
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 92
caaactggtg gtggttggag caggtgatgt tgggaaaagc gcactgacaa tcc         53

<210> SEQ ID NO 93
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 93
ggattgtcag tgcgcttttc ccaacacgac ctgctccaac caccaccagt ttg         53

<210> SEQ ID NO 94
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 94
gttggacata ctggatacag ctggacaaga agagtacagt gccatgagag acc         53

<210> SEQ ID NO 95
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 95
ggtctctcat ggcactgtac tcttcttgtc cagctgtatc cagtatgtcc aac         53

<210> SEQ ID NO 96
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 96
gttggacata ctggatacag ctggaaaaga agagtacagt gccatgagag acc         53

<210> SEQ ID NO 97
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 97
ggtctctcat ggcactgtac tcttctcgtc cagctgtatc cagtatgtcc aac         53

<210> SEQ ID NO 98
<211> LENGTH: 53

```
<212> TYPE: DNA
<213> ORGANISM: Artificial Sequence
<220> FEATURE:
<223> OTHER INFORMATION: Synthetic Oligonucleotide

<400> SEQUENCE: 98
ggtctctcat ggcactgtac tcttctagtc cagctgtatc cagtatgtcc aac        53

<210> SEQ ID NO 99
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 99
gttggacata ctggatacag ctggacacga agagtacagt gccatgagag acc        53

<210> SEQ ID NO 100
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 100
gttggacata ctggatacag ctggacatga agagtacagt gccatgagag acc        53

<210> SEQ ID NO 101
<211> LENGTH: 140
<212> TYPE: DNA
<213> ORGANISM: Artificial Sequence
<220> FEATURE:
<223> OTHER INFORMATION: BRAF Exon 11

<400> SEQUENCE: 101
gtgatgattg ggagattcct gatgggcaga ttacagtggg acaaagaatt ggatctggat    60
catttggaac agtctacaag ggaaagtggc atggtgatgt ggcagtgaaa atgttgaatg    120
tgacagcacc tacacctcag                                                140

<210> SEQ ID NO 102
<211> LENGTH: 210
<212> TYPE: DNA
<213> ORGANISM: Artificial Sequence
<220> FEATURE:
<223> OTHER INFORMATION: BRAF Exon 15

<400> SEQUENCE: 102
atggattact tacacgccaa gtcaatcatc cacagagacc tcaagagtaa taatatattt    60
cttcatgaag acctcacagt aaaaataggt gattttggtc tagctacagt gaaatctcga    120
tggagtgggt cccatcagtt tgaacagttg tctggatcca ttttgtggat ggcaccagaa    180
gtcatcagaa tgcaagataa aaatccatac                                     210

<210> SEQ ID NO 103
<211> LENGTH: 210
<212> TYPE: DNA
<213> ORGANISM: Artificial Sequence
<220> FEATURE:
<223> OTHER INFORMATION: NRAs Exon 2

<400> SEQUENCE: 103
ttactggttt ccaacaggtt cttgctggtg tgaaatgact gagtacaaac tggtggtggt    60
```

```
tggagcaggt ggtgttggga aaagcgcact gacaatccag ctaatccaga accactttgt    120
agatgaatat gatcccacca tagaggtgag gcccagtggt agcccgctga cctgatcctg    180
tctctcactt gtcggatcat ctttacccat                                    210

<210> SEQ ID NO 104
<211> LENGTH: 140
<212> TYPE: DNA
<213> ORGANISM: Artificial Sequence
<220> FEATURE:
<223> OTHER INFORMATION: NRAS Exon 3

<400> SEQUENCE: 104
atagatggtg aaacctgttt gttggacata ctggatacag ctggacaaga agagtacagt    60
gccatgagag accaatacat gaggacaggc gaaggcttcc tctgtgtatt tgccatcaat    120
aatagcaagt catttgcgga                                               140

<210> SEQ ID NO 105
<211> LENGTH: 280
<212> TYPE: DNA
<213> ORGANISM: Artificial Sequence
<220> FEATURE:
<223> OTHER INFORMATION: KRAs Exon 2

<400> SEQUENCE: 105
tagtgtatta accttatgtg tgacatgttc taatatagtc acattttcat tatttttatt    60
ataaggcctg ctgaaaatga ctgaatataa acttgtggta gttggagctg gtggcgtagg    120
caagagtgcc ttgacgatac agctaattca gaatcatttt gtggacgaat atgatccaac    180
aatagaggta aatcttgttt taatatgcat attactggtg caggaccatt ctttgataca    240
gataaaggtt tctctgacca ttttcatgag tacttattac                         280

<210> SEQ ID NO 106
<211> LENGTH: 280
<212> TYPE: DNA
<213> ORGANISM: Artificial Sequence
<220> FEATURE:
<223> OTHER INFORMATION: KRAs Exon 3

<400> SEQUENCE: 106
ccttttttga gtaaaaggt gcactgtaat aatccagact gtgtttctcc cttctcagga    60
ttcctacagg aagcaagtag taattgatgg agaaacctgt ctcttggata ttctcgacac    120
agcaggtcaa gaggagtaca gtgcaatgag ggaccagtac atgaggactg gggagggctt    180
tctttgtgta tttgccataa ataatactaa atcatttgaa gatattcacc attataggtg    240
ggtttaaatt gaatataata agctgacatt aaggagtaat                         280

<210> SEQ ID NO 107
<211> LENGTH: 180
<212> TYPE: DNA
<213> ORGANISM: Artificial Sequence
<220> FEATURE:
<223> OTHER INFORMATION: KRAs Exon 4

<400> SEQUENCE: 107
gaaataaatg tgatttgcct tctagaacag tagacacaaa acaggctcag gacttagcaa    60
gaagttatgg aattccttttt attgaaacat cagcaaagac aagacaggta agtaacactg    120
aaataaatac agatctgttt tctgcaaaat cataactgtt atgtcattta atatatcagt    180
```

METHODS AND COMPOSITIONS FOR TREATING CANCER BY IDENTIFYING ONE OR MORE ERK MUTATIONS

FIELD OF THE INVENTION

This invention relates to methods for the detection of genetic mutations and uses thereof for the treatment of cancer.

BACKGROUND OF THE INVENTION

The processes involved in tumor growth, progression, and metastasis are mediated by signaling pathways that are activated in cancer cells. The mitogen-activated protein kinase (MAPK) pathway, of which extracellular regulated kinase (ERK) is a downstream member, plays a central role in regulating mammalian cell growth by relaying extracellular signals from ligand-bound cell surface tyrosine kinase receptors such as erbB family, PDGF, FGF, and VEGF receptor tyrosine kinase. Activation of the MAPK/ERK pathway is via a cascade of phosphorylation events that begins with activation of a small guanosine triphosphatase (GTPase), RAS. Activation of RAS leads to the recruitment and activation of RAF, a serine-threonine kinase. Activated RAF then phosphorylates and activates MEK1/2, which in turn phosphorylates and activates ERK1/2. When activated, ERK1/2 phosphorylates several downstream targets involved in a multitude of cellular events including cytoskeletal changes and transcriptional activation.

The MAPK/ERK pathway is one of the most important for cell proliferation and it is believed that this pathway is frequently activated in many tumors. RAS genes, which are upstream of ERK1/2, are mutated in several cancers including colorectal, melanoma, breast and pancreatic tumors. The high RAS activity is accompanied by elevated ERK activity in many human tumors. In addition, mutations of BRAF, a serine-threonine kinase of the RAF family, are associated with increased kinase activity. Mutations in BRAF have been identified in melanomas (60%) (Fecher, L. A., et al., *Curr. Opin. Oncol.*, 2008, 20:183-189), thyroid cancers (approximately 50%) (Robert, R. J., and Der, C. J., *Oncogene*, 2007, 26: 329103310), and colorectal cancers (Davies, H., et al., *Nature*, 2002, 417: 949-954; Kohno, M., and Pauyssegur, J., *Ann. Med.*, 2006, 38: 200-211).

KRAS also acts upstream of ERK to regulate proliferation, differentiation, and cell survival. Mutations in codons 12, 13, and 61 of KRAS result in constitutive growth signaling and confers resistance to compounds targeting the EGFR signaling pathway (Andre, T., et al., *Annals of Oncology*, 2012, 00: 1-8; DeRook, W., et al., *Lancit Oncology*, 2010, 11: 6753-6762). KRAS mutations are found in 65% of pancreatic cancers, 40% of colon cancers, 20% of lung cancers, and 10% of gastric cancers (Downward, J., *Nat. Rev. Cancer*, 2003, 3: 11-22; Smalley, K. S. M., *Int. J. Cancer*, 2003, 204: 527-532). Most patients with KRAS mutations in codons 12, 13, and/or 61 do not respond well to anti-EGFR monoclonal antibody (mAb) therapies (Lièvre, A., et al., *Cancer Res.*, 2006, 66(8):3992-3995).

The mutational status of solid tumors is also becoming increasingly important for identifying the best treatment options for cancer patients (Yokota, T., *Anti-Cancer Agents in Medicinal Chemistry*, 2012, 12: 163-171). Treatments developed targeting a specific signaling pathway may not be effective when activating mutations are present downstream of the signal transduction pathway. For example, tumors harboring activating mutations in RAS and RAF do not generally respond well to anti-EGFR therapy, in that these mutations are believed to lead to EGFR-independent activation of an intracellular signaling pathway (Messersmith, W. A., and Ahnen, D. J., *N. Engl., J. Med.*, 2008, 359(17): 1834-1836). As such, it is believed that inhibitors targeting proteins further downstream in this pathway may be more effective in treating these cancers.

As such, proteins that lie downstream of RAS and, even further downstream of RAF and MEK, in the MAPK/ERK pathway are potential targets for pharmacological intervention (Downward, J., *Nat. Rev. Cancer*, 2003, 3: 11-22; Pearson, G., et al., *Endocr. Rev.*, 2001, 22: 153-183; Fecher, L. A., et al., *Curr. Opin. Oncol.*, 2008, 20: 183-189). Gain of function, i.e., activating, mutations in RAS and RAF that lead to constitutive activation of this pathway are frequently observed in human cancers and are associated with high rates of cancer cell proliferation (Id.). It has been reported that activating mutations of RAS were identified in about 25% of all cancers (Smalley, K. S. M., *Int. J. Cancer*, 2003, 104: 527-532). These mutations, especially for KRAS, are present at even higher rates in pancreatic cancer and colorectal cancer (KRAS$^+$ in 90% and 50%, respectively, Downward, 2003, and Smalley, 2003). Other studies also reported that NRAS mutations were detected in about 10% to 25% of melanomas (Downward, 2003; Fecher, 2008; Smalley, 2003; Robert, P. J., and Der, C. J., *Oncogene*, 2007, 26: 3291-3310) and KRAS mutations were detected in about 30% non-small cell lung cancers (NSCLCs) (Downward, 2003; Wistuba, I. I., et al., *Semin. Oncol.*, 2001, 28(2)(suppl 4): 3-13). In addition, RAS mutations (HRAS, KRAS, or NRAS) have been identified in about 55% to 60% of thyroid cancers (Fecher, 2008).

Similarly, BRAF mutations have been identified in about 60% of malignant melanomas, where all mutations appear to be within the kinase domain and a single substitution (T→A, V600E) accounts for about 80% of the mutations (Davies, H., et al., *Nature*, 2002, 417: 949-954; Kohno, M., and Pouyssegur, J., *Ann. Med.*, 2006, 38: 200-211). Activating BRAF mutations have also been documented in a variety of human cancers other than melanoma, including about 10% in colorectal cancer (CRC), approximately 50% in thyroid cancer (Roberts and Der, 2007), and several percent in NSCLC (Brose, M. S., et al., Cancer Res., 2002, 62: 6997-7000). The high frequency of RAS or BRAF mutations in these cancers makes targeting this pathway an attractive strategy for new anti-cancer agents that rely on patient stratification to identify individuals most likely to benefit from inhibitors that target the MAPK/ERK pathway (Pratilas, C. A., and Solit, D. B., *Rev. Recent Clin. Trials*, 2007, 2: 121-134).

Scientific and clinical attention has recently focused on the major mutational hotspots in these genes (KRAS codons 12, 13 and 61 and BRAF 600). However, there is increasing evidence that mutations in other locations can also lead to a tumorigenic phenotype (Andre, T., et al., *Annals of Oncology*, 2012, 00:1-8; DeRook, W., et al., *Lancit Oncology*, 2010, 11: 6753-6762).

Sanger sequencing, a method of DNA sequencing based on the selective incorporation of chain terminating dideoxynucleotides by DNA polymerase during in vitro DNA replication, considered to be the "gold standard" for detecting genetic mutations, is generally considered not sensitive enough to detect genetic mutations present at low level or low copy number relative to wild type DNA. Commercially available BRAF and KRAS kits, such as, TheraScreen® (CE-IVD) KRAS Mutation kit (DxS Ltd., Manchester, UK) and the FDA approved Cobas® KRAS and BRAF Mutation Test kits (Roche Diagnostics, Indianapolis, Ind.) for testing mutations in codons 12, 13, and 61 of KRAS and the BRAF V600E mutation, respectively, detect mutations only at limited locations. The TheraScreen® KRAS assay is based on real-time PCR Scorpion and ARMS technologies that detects seven frequently encountered mutations in codon 12 and 13 (Angulo, B., et al., *J. Mol. Diagn.*, 2010 May 12(3): 292-299). The Cobas® KRAS Mutation assay, a TaqMelt PCR assay, reports only mutations in general to codon 12/13 or 61, but not specific mutations needed for exploratory data analysis. The Cobas® BRAF Mutation assay only detects the single BRAF V600E mutation. There is currently no commercial NRAS mutation detection assay.

SUMMARY OF THE INVENTION

The instant invention relates generally to methods for the detection of MAPK/ERK pathway mutations. In one embodiment, the invention comprises a sensitive and selective assay capable of detecting MAPK/ERK pathway mutations, specifically to BRAF, KRAS, and NRAS, and hereinafter referred to as an "ERK Mutation," at more than 30 "hotspots" or loci. In another aspect of this embodiment, the invention comprises primers and probes for the detection of the BRAF, KRAS, and NRAS mutations in a single reaction.

In another embodiment, the invention comprises a method to identify and select patients diagnosed with cancer for treatment with an ERK inhibitor, wherein said patients to be treated have one or more ERK Mutations. In another aspect of this embodiment, the invention comprises a method to treat a patient, having one or more mutations to BRAF, KRAS, and NRAS, with an ERK inhibitor.

BRIEF DESCRIPTION OF THE DRAWINGS

FIGS. 6A-6C illustrate the PCR primer locations and hotspots for BRAF (FIG. 6A), NRAS (FIG. 6B), and KRAS (FIG. 6C). The portion of the sequence highlighted in dark gray denotes the location of the PCR primers, while the portion highlighted in light gray are hot spot codons around which the SNPE probes were designed.

DETAILED DESCRIPTION OF THE INVENTION

Figure 1:
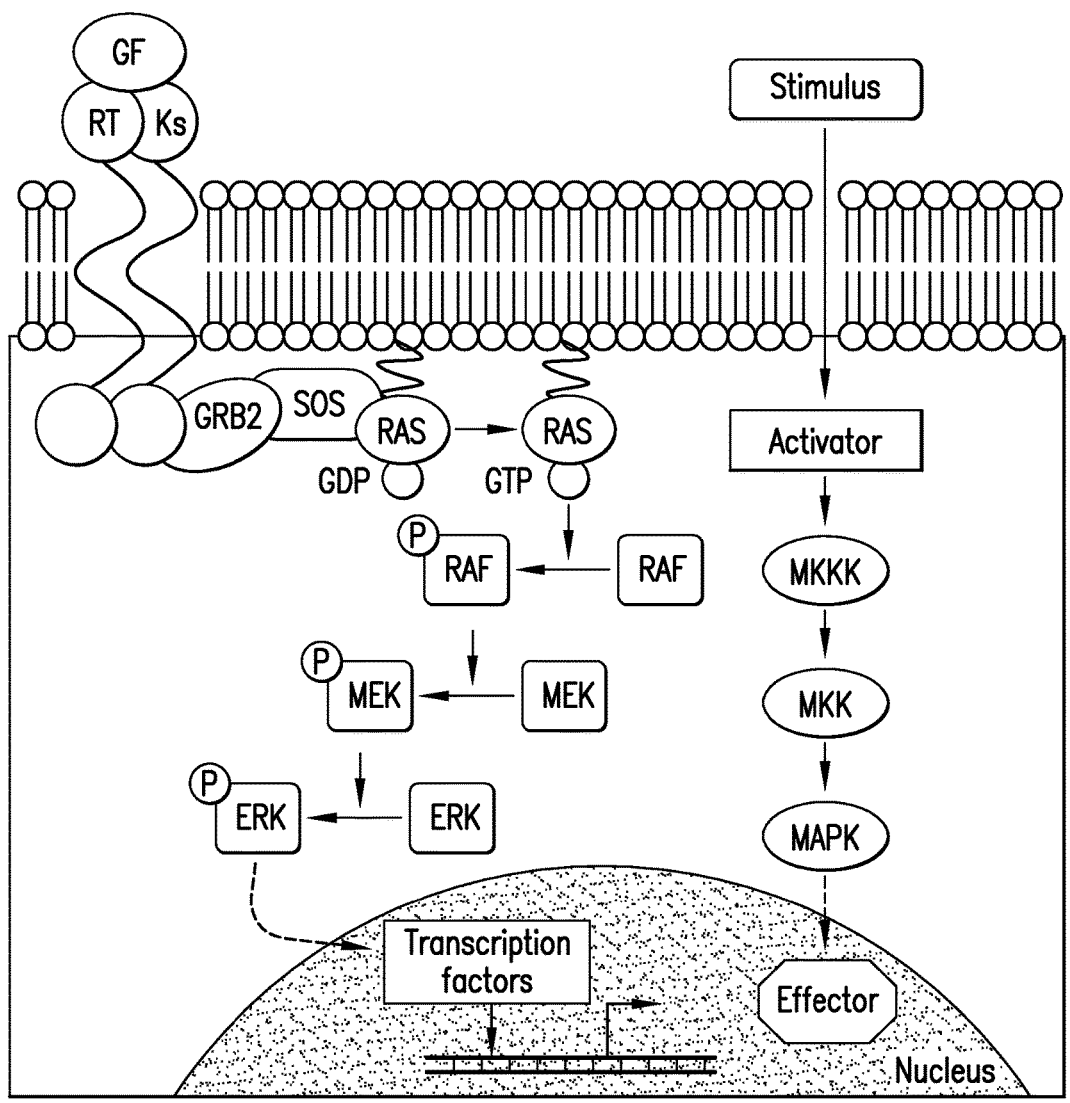
FIG. 1 is a graphic illustration of the pathway for the growth and differentiation factor, ERK, showing the relationship of ERK to the RAS and RAF genes in the MAPK pathway (Kabbarah, O., and Chin, L., *Frontiers in Bioscience*, 2006, 11:928-942).
Figure 2A:
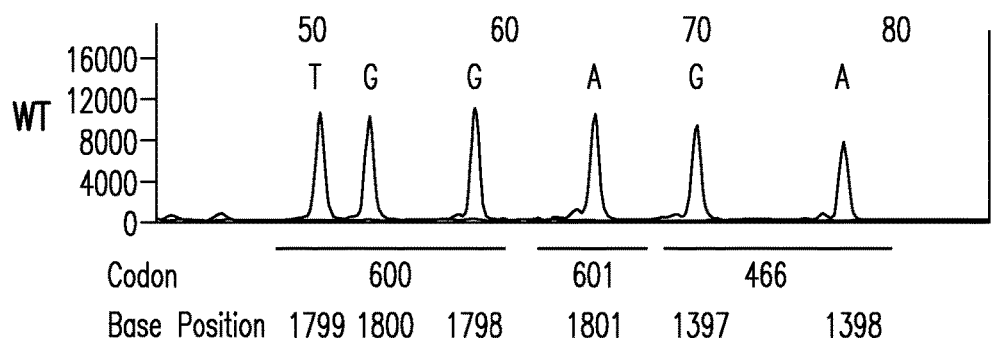
FIGS. 2A-2C are graphics illustrating the ERK Mutation Assay results for the BRAF Probe Pool 7: wild type (WT) control (FIG. 2A); V600E mutation (MT) (FIG. 2B); and the V600D mutation (MT) (FIG. 2C). The position of the codons and nucleotides are indicated at the bottom of the figure. The nucleotide label for each peak has been converted to the sense strand.
Figure 2B:
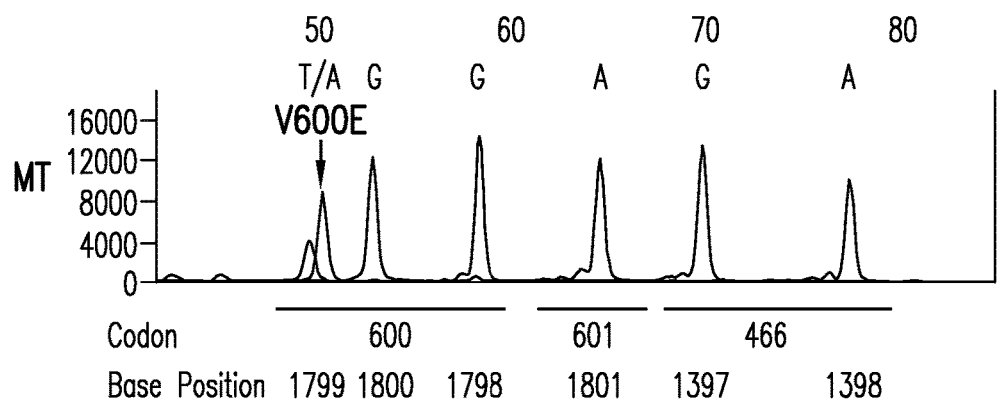
Figure 2C:
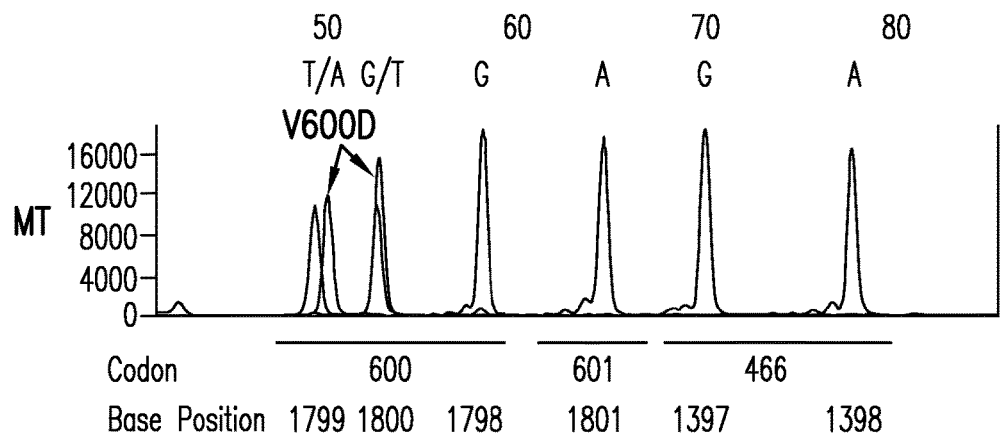
Figure 3:
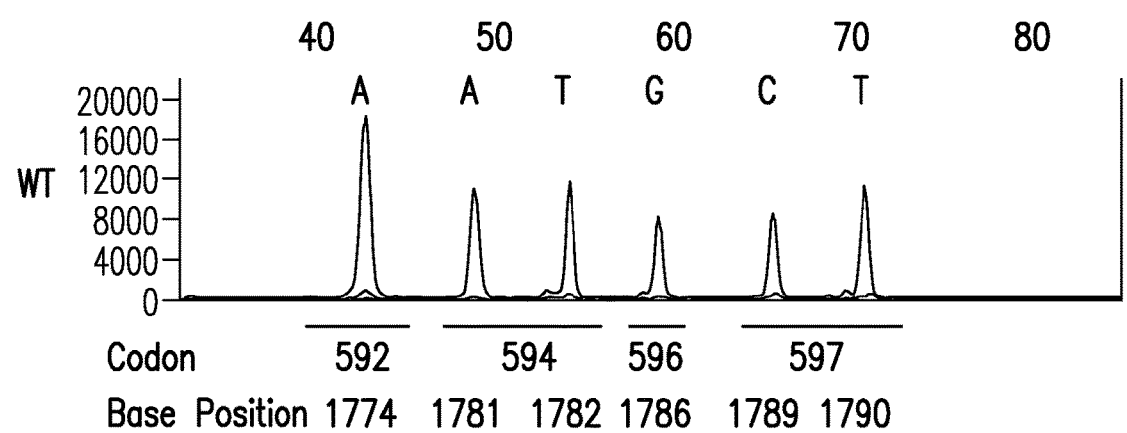
FIG. 3 is a graphic illustrating the ERK Mutation Assay results for the BRAF Probe Pool 6: wild type (WT) control. The position of the codons and nucleotides are indicated at the bottom of the figure. The nucleotide label for each peak has been converted to the sense strand.
Figure 4A:
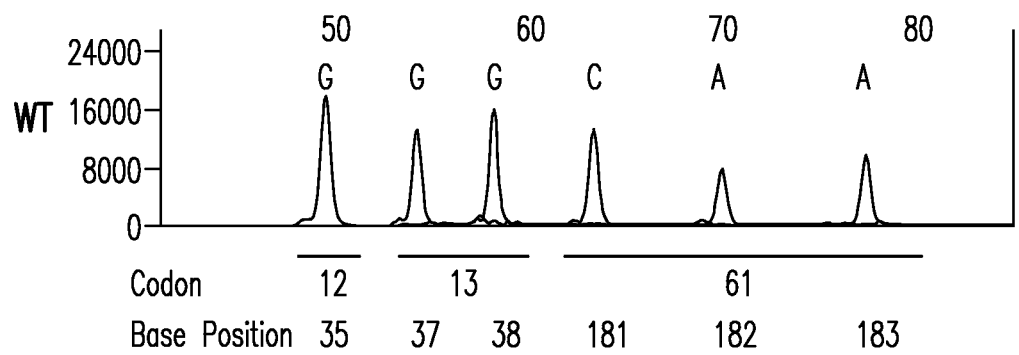
FIGS. 4A-4C are graphics illustrating the ERK Mutation Assay results for the NRAS Probe Pool: wild type (WT) control (FIG. 4A); Q61K mutation (MT) (FIG. 4B); and the Q61L mutation (MT) (FIG. 4C). The position of the codons and nucleotides are indicated at the bottom of the figure. The nucleotide label for each peak has been converted to the sense strand.
Figure 4B:
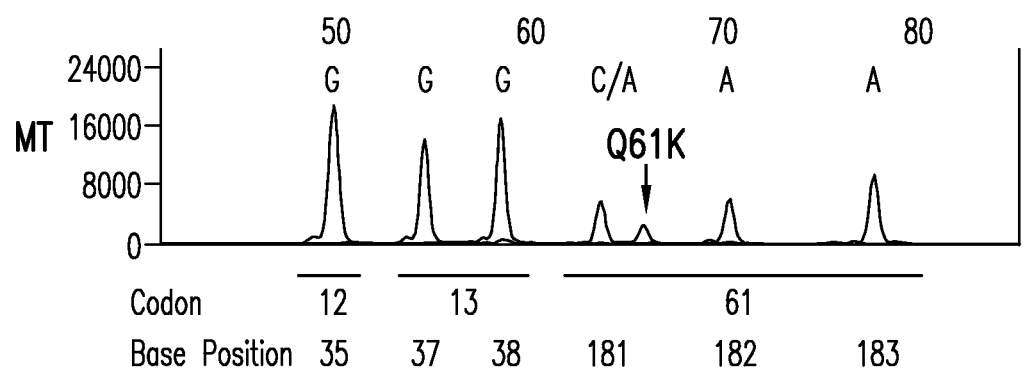
Figure 4C:
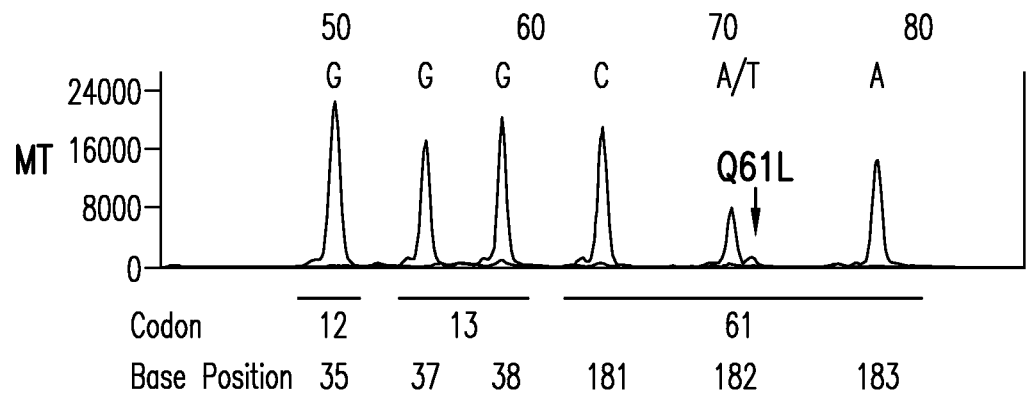

The invention herein relates to the field of nucleic acid sequence detection. Nucleic acid sequence detection can be used to determine the presence or absence of a particular genetic element or it can be used to determine the specific type of a particular genetic element that is present. The detection of nucleic acids in a sample and the subtypes thereof typically rely on the technique of specific nucleic acid hybridization, which are based on the tendency of two nucleic acid strands to pair at complementary regions. Nucleic acid hybridization assays are used to detect and identify unique DNA and RNA base sequences or specific genes in a complete DNA molecule in mixtures of nucleic acid, or in mixtures of nucleic acid fragments.

The practical use of nucleic acid hybridization assays was greatly enhanced by methods that included amplifying or copying, with fidelity, precise sequences of nucleic acid found at low concentration to higher copy numbers, so as to make them more readily detectable. The original amplification method is the polymerase chain reaction described by Mullis, et al., U.S. Pat. Nos. 4,683,195; 4,683,202; and 4,965,188. Further improvements in the use of these assays was the introduction of multiplex assays, that allowed for the simultaneous amplification and detection of multiple nucleic acid target sequences through the use of optimized primers and reaction conditions. Commercial kits are available to carry out these multiplex hybridization assays. One such kit, the SNaPshot™ Multiplex Kit can be used to carry out a nucleic acid hybridization assay that can detect and identify single nucleotide polymorphisms (SNPs) at known locations on DNA templates (Larkin, I., et al., 2010, *PLoS ONE* 5: e8802; Dias-Santagata, D., et al., 2011, *PLoS ONE* 6:e17948). The kit includes a reaction mix, comprising a DNA polymerase, fluorescent labels, and a reaction buffer, a control primer mix, comprising one or more primers for control reactions, and a control template. The chemistry of the kit is based on the dideoxy single-base extension of an unlabeled oligonucleotide primer (or primers). Each primer binds to a complementary template in the presence of fluorescently labeled ddNTPs and the DNA polymerase. The oligonucleotide probes are designed to hybridize immediately adjacent to the 3' side of the nucleotides of interest. The DNA polymerase probe is extended by the addition of a single fluorescently labeled dideoxynucleotide. The detection of the mutation is made by a combination of the identification of the fluorescently tagged nucleotide added and the size migration of the probe during capillary electrophoresis.

A PCR-based approach to detect all of the mutations to KRAS, BRAF, and NRAS would likely require more than 100 primer/probe sets and at least 30 individual reactions. Qualitative mutant-enriched PCR assays are commercially available, such as the KRAS StripAssay® (ViennaLab, Vienna, Austria), and they appear to be sensitive enough to detect low mutant copies (Sarasquenta, A. F., et al., *J. Mol. Diag.*, 2011, 13(2):199-205), but these commercial tests require the use of a large number of evaluations/assays to detect all of the mutations and they provide no estimate of frequency for individual mutations in the corresponding sample, i.e., only yes (presence) or no (absence) answers as to the mutation are obtained. However, many treatment responses appear to be directly correlated to the mutation frequency for the mutant population detected in the wild-type background (unpublished data). Such information, when analyzed retrospectively, adds value to the final evaluation of a clinical trial and for the interpretation of patient treatment response.

In that there is a lack of viable options to the standard PCR approach for clinical use, Applicants herein have developed and validated an efficient semi-quantitative multiplexed assay, referred to herein as the KRAS/BRAF/NRAS single nucleotide primer extension assay (KBN-SNPE assay) or, alternatively, as the ERK Mutation Assay, to detect a broader array of mutations to these genes. The ERK Mutation Assay employs a limited number of primers (14, Table 1) and probes (28, Table 2), capable of detecting single point polymorphism mutations for the KRAS, BRAF, and NRAS genes in this pathway in a single reaction. As such, this assay can be used as a high throughput screening assay for drug development or as a clinical, functional use assay, to identify and/or select patients diagnosed with cancer having an ERK Mutation for treatment with an ERK inhibitor.

DEFINITIONS

"ERK Mutation" means a genetic mutation in a gene which encodes a protein in the MAPK pathway to which ERK is a downstream member. As used herein, this term means generically any mutation to KRAS, BRAF, and NRAS in the MAPK/ERK pathway and specifically those mutations identified in Table 5.

"ERK inhibitor" means any compound or agent that inhibits or affects the activity of an ERK protein, including ERK1 and ERK2, either directly or indirectly, such as, via inhibition or affecting the activity of a member of the MAPK pathway to which ERK is a downstream member. Members of the MAPK/ERK pathway include BRAF, KRAS, and NRAS. Such molecules would be useful for treating a broad spectrum of cancers, such as, for example, melanoma, pancreatic cancer, thyroid cancer, colorectal cancer, lung cancer, breast cancer, and ovarian cancer. Examples of small molecule ERK inhibitors useful for the treatment of such cancers are described in WO 2011/16330, which are incorporated herein by reference as if set forth at length. PCT publications WO 2007/070398 and WO 2008/153858 disclose polycyclic indazole derivatives that are useful as ERK inhibitors for the treatment of cancer.

"ERK Mutation Assay" means the KRAS/BRAF/NRAS single nucleotide primer extension assay (ERK MUTATION assay) described herein used to detect and quantify an ERK Mutation.

The invention herein is a multiplex nucleic acid hybridization assay, herein referred to as the ERK Mutation assay, which allows for the specific detection and identification of over 30 mutations in the BRAF, KRAS, and NRAS genes, all members of the MAPK/ERK pathway, thought to activate or increase the activity of the MAPK/ERK pathway. Current commercially available assays target a small subset, typically 1-7 each, of the known mutations to KRAS and BRAF, which enables detection of roughly 80% of the known mutations. Moreover, the currently available assays can target the mutations of only one gene per reaction. The ERK Mutation Assay is a single nucleotide primer extension (SNPE) multiplexed assay consisting of multiplexed oligonucleotide primer extension reactions that determine the nucleotide sequence at 27 hot spot locations in the KRAS, BRAF and NRAS genes. Each reaction consists of multiplexed oligonucleotide primer extension reactions. BRAF consists of thirteen oligonucleotide probes, multiplexed in separate reactions of six and seven probes, respectively, while KRAS and NRAS are multiplexed in separate reactions with nine and six probes, respectively.

The ERK Mutation Assay includes multiplexing of both the PCR template amplifications and the Single Nucleotide Primer Extension (SNPE) reactions, using the PCR primers of Table 1 (SEQ ID NOS: 1-14) and the SNPE probes of Table 2 (SEQ ID NOS: 15-42). Thus, the competition among the PCR primers is not only against the gDNA templates, but also against each other. These primers also compete against nucleotides and DNA polymerase both in the kinetic and thermodynamic manner depending on their size, sequence, and melting temperature.

In one embodiment, the invention comprises the ERK Mutation Assay for detecting and identifying an ERK Mutation comprising:

(a) contacting a biological sample from a patient diagnosed with cancer with a plurality of polymerase chain reaction (PCR) primers selected from the group consisting of the PCR primers of Table 1 (SEQ ID NO: 1-14), which target one or more ERK Mutations;

(b) amplifying the section of said sample targeted by the PCR primers to form a PCR template containing one or more targeted ERK Mutations;

(c) contacting the PCR template of step (b) with a plurality of single nucleotide primer extension (SNPE) probes, selected from the group consisting of the SNPE probes of Table 2 (SEQ ID NO: 15-42), under hybridization conditions suitable to form a duplex between the template and the SNPE probe, such that the nucleotide base to be identified is the first unpaired base in the template immediately downstream of the 3' end of the probe in said duplex;

(d) contacting the PCR template-SNPE duplex of step (c) with i) a reaction mixture comprising a DNA polymerase and a mixture of ddNTPs terminators of a nucleic acid template-dependent primer extension reaction, wherein each terminator is capable of specifically terminating the extension reaction in a manner strictly dependent on the identity of the unpaired nucleotide base in the targeted ERK Mutation PCR template immediately downstream of the 3' end of the primer, wherein each terminator in the mixture is complementary to the nucleotide base to be identified, and wherein each terminator is labeled with a detectable marker,
ii) under conditions sufficient to carry out a template-dependent primer extension reaction to form an SNPE product, wherein said conditions permit the base pairing of the complementary terminator with the nucleotide base to be identified and the incorporation of the complementary terminator onto the 3' end of the primer to thereby extend said 3' end of the primer by one terminator; and (e) determining the presence and identity of the nucleotide base at the specific position in the SNPE product by detecting the detectable marker of the incorporated terminator of step (d) while said terminator is incorporated at the 3' end of the extended primer, and wherein the ERK Mutation is determined by the identified nucleotide base at the specific position in the SNPE product.

In another embodiment, the invention comprises the ERK Mutation Assay for detecting and identifying an ERK Mutation comprising:

(a) contacting a biological sample from a patient diagnosed with cancer with a plurality of polymerase chain reaction (PCR) primers selected from the group consisting of the PCR primers of Table 1 (SEQ ID NOs: 1-14), which target one or more ERK Mutations;

(b) amplifying the section of said sample targeted by the PCR primers to form a PCR template containing one or more targeted ERK Mutations;

(c) contacting the PCR template of step (b) with a plurality of single nucleotide primer extension (SNPE) probes, selected from the group consisting of the SNPE probes of Table 2 (SEQ ID NO: 15-42), under hybridization conditions suitable to form a duplex between the template and the SNPE probe, such that the first unpaired nucleotide base in the template immediately downstream of the 3' end of the probe in said duplex is a nucleotide base to be identified, wherein the nucleotide base to be identified is an ERK Mutation;

(d) contacting the PCR template-SNPE duplex of step (c) with (i) a reaction mixture comprising a DNA polymerase; and (ii) a mixture of ddNTP terminators of a nucleic acid template-dependent primer extension reaction, wherein each terminator is capable of specifically terminating the extension reaction in a manner strictly dependent on the identity of the unpaired nucleotide base in the PCR template that is immediately downstream of the 3' end of the primer, wherein each terminator in the mixture is complementary to the nucleotide base to be identified, and wherein each terminator is labeled with a detectable marker;

under conditions sufficient to carry out a template-dependent primer extension reaction to form an SNPE product, wherein said conditions permit base pairing of a complementary terminator with the nucleotide base to be identified and incorporation of the complementary terminator onto the 3' end of the primer, thereby extending said 3' end of the primer by one terminator;

(e) determining the presence and identity of the nucleotide base to be identified at the specific position in the SNPE product by detecting the detectable marker of the incorporated terminator of step (d) while said terminator is incorporated at the 3' end of the extended primer.

In one aspect of this embodiment, in step (d) of the method, the ddNTP terminators are a mixture of ddATP, ddCTP, ddGTP, and ddTTP. In another aspect of this embodiment, the ddNTP terminators are detectably labeled, each with a different detectable label.

In another embodiment, the invention is the use of the ERK Mutation Assay to identify and select a patient diagnosed with cancer to be treated with an ERK inhibitor, wherein the patient identified for treatment has one or more ERK Mutations. In one aspect of this embodiment, the patient identified for treatment has one or more KRAS, BRAF, or NRAS mutations. In another aspect of this embodiment, the patient identified for treatment has one or more of the mutations listed in Table 5.

In still another embodiment, the invention is a method of treating a patient diagnosed with cancer with an ERK inhibitor, wherein the patient to be treated is characterized as having one or more ERK Mutations, and wherein the ERK Mutation is detected and identified using the ERK Mutation Assay. In one aspect of this embodiment, the patient to be treated with the ERK inhibitor has one or more KRAS, BRAF, or NRAS mutations that are detected and identified using the ERK Mutation assay. In another aspect of this embodiment, the patient to be treated with the ERK inhibitor has one or more of the mutations listed in Table 5 that are detected and identified using the ERK Mutation assay.

In yet another embodiment, the invention is a kit to detect and identify an ERK Mutation in a patient diagnosed with cancer. In one aspect of this embodiment, the kit includes the PCR primers of Table 1 (SEQ ID NOS: 1-14) and the SNPE probes of Table 2 (SEQ ID NOS: 15-42). In another aspect of this embodiment, the kit is used in a clinical setting to identify and select patients for treatment with an ERK inhibitor.

Any DNA sample may be used to carry out the present invention. The DNA may be obtained from any type of biological sample, including but not limited to, tissue or body fluid samples, such as, blood, plasma, or cerebral spinal fluid. In one embodiment, the inventive assay used genomic DNA obtained from a tissue sample, specifically, from a formalin-fixed paraffin embedded (FFPE) tissue sample obtained from a patient diagnosed with cancer. The DNA sample may be extracted from the biological sample using any of the numerous methods that are standard in the art. Those skilled in the art would understand and recognize that the method to be used will depend on the nature of the source of the sample. The amount of DNA to be extracted for use in the present invention will depend on the nature of the source of the sample, but is typically at least 5 ng. In one embodiment, the amount used by the Applicants was 15 ng. The DNA sample to be used in the inventive assay can be single or double-stranded. Those skilled in the art would recognize and appreciate that the standard conditions utilized while carrying out a polymerase chain reaction type reaction would typically be sufficient to separate double-stranded DNA into single-stranded DNA for purposes of the reaction.

In one embodiment of the invention, the method uses a plurality of polymerase chain reaction (PCR) primers selected from the group of PCR primers listed in Table 1 (SEQ ID NOS: 1-14). Those skilled in the art would understand that a forward and reverse primer specific to each target or region to be amplified is needed to carry out a polymerase chain reaction to generate the templates for the SNPE assay. Thus, the inventive method employs the use of multiple pairs of PCR primers in order to generate the templates, containing the hotspots or targets, for each target gene, i.e. KRAS, NRAS, and BRAF.

Similarly, in one embodiment of the invention, the method uses a plurality of SNPE probes selected from the SNPE probes listed in Table 2 (SEQ ID NOS: 15-42). Those skilled in the art would understand that while the SNPE probes target a specific ERK Mutation gene, i.e. KRAS, NRAS, or BRAF, unlike other PCR-based mutation detection methods that require a separate probe for the detection of each possible mutation, the inventive SNPE probes listed in Table 2 (SEQ ID NOS: 15-42) have been designed such that they will detect multiple mutations occurring at the same hot spot or loci. Those skilled in the art would also understand that there are limits to the number of probes, typically 10-12, that can be used per reaction in a multiplex/SNPE assay. Thus, the inventive SNPE probes not only reduce the number of SNPE probes needed to detect virtually any mutation occurring at the ERK gene hotspots, they allow for the detection of multiple mutations in all three ERK genes in one reaction. In one embodiment, the inventive method uses 9 KRAS probes, 6 NRAS probes, and 13 BRAF probes, broken down into two groups of 6 and 7 probes, BRAF-1 and BRAF-2, respectively (Table 2) (SEQ ID NOS: 15-42), to detect multiple mutations across the three genes in one reaction. In another aspect of this embodiment, the inventive method can be utilized as a high throughput screening assay.

In practicing the invention, those skilled in the art would understand that prior to determining the presence and identity of the nucleotide base at the specific position in the primer extended reaction product, that the reaction product is denatured, using standard techniques known in the art, prior to loading onto a DNA sequencer for separation, detection, and identification. Further, those skilled in the art would also understand that the detection and identification of the nucleotide base at a specified position is based on standard techniques, such as the color and size of the incorporated labeled ddNTP and probe used in the reaction. As used herein, the inventive assay used a mixture of labeled ddATP, ddCTP, ddGTP, and ddTTP, each of which was labeled with a different detectable label, with the specified reaction probes (Table 2) (SEQ ID NOS: 15-42), which enables the detection and identification of the nucleotide in question based on color, i.e. identifies which nucleotide was incorporated, and size, i.e. the length of the tail on the probe.

EXAMPLES

Example 1

Cell Lines and Formalin-Fixed Paraffin Embedded (FFPE) Samples

All cell lines were obtained from American Type Culture Collection (ATCC) (Manassas, Va.) and cultivated using recommended conditions. Genomic DNA (gDNA) was extracted from cell pellets using a DNeasy Blood and Tissue Kit (Qiagen, Germantown, Md.). Sixty formalin-fixed paraffin embedded (FFPE) samples, ten FFPE slides each, from the following cases of human cancers were purchased from BioChain's repository network (Newark, Calif.): colorectal, melanoma, ovarian, thyroid, pancreatic, and lung (non-small cell lung cancers). Tissue samples were immediately fixed in formalin and paraffin embedded. Five micron thick sections were cut and mounted on positively charged slides. FFPE samples were shipped at room temperature and stored at 4-8° C. Extraction of gDNA from FFPE tissue samples was performed using the Qiagen DNA FFPE Tissue Extraction Kit (Qiagen, Germantown, Md.) following manufactures instructions. Briefly, the excess paraffin was removed from one or two 5 micron thick sections and the tissue scraped off the slide using a fresh surgical scalpel. A new scalpel was used for each section. The paraffin was removed by successive washes with xylene and ethanol and the tissue digested with proteinase K. The released gDNA was bound and eluted from a miniElute column (Qiagen, Germantown, Md.) in 50 µL, quantified using a NanoDrop spectrometer (NanoDrop Products, Wilmington, Del.) and adjusted to a concentration of 5 ng/µL and stored at −80° C.

Example 2

PCR Primers and Single Nucleotide Primer Extension (SNPE) Probes and Synthetic Oligonucleotides PCR primers (Table 1), SNPE probes (Table 2) and synthetic oligonucleotides (Table 3) were prepared by Sigma (St. Louis, Mo.) based on Applicants design and were either desalted or purified by HPLC. Except where noted, all reagents for the polymerase chain reaction (PCR) and single nucleotide primer extension (SNPE) reactions were obtained from ABI-Life Technologies (Carlsbad, Calif.).

PCR primer sequences (Table 1) (SEQ ID NOS:1-14) were designed by Applicants to amplify gene fragments ranging in size from 100-150 nucleotides of the hot spot regions of KRAS, NRAS and BRAF. To accomplish this, DNA sequences surrounding the regions of interest were manually scanned to identify portions which could serve as primers to amplify the appropriately sized fragment of DNA (FIGS. 6A-6C). BLAST searches with the amplified regions were performed to confirm specificity of the PCR amplified product. Because individual exons were not equally amplified during the PCR amplification step, the concentration of the various PCR primers was adjusted until all exons were equally amplified.

Figure 7:
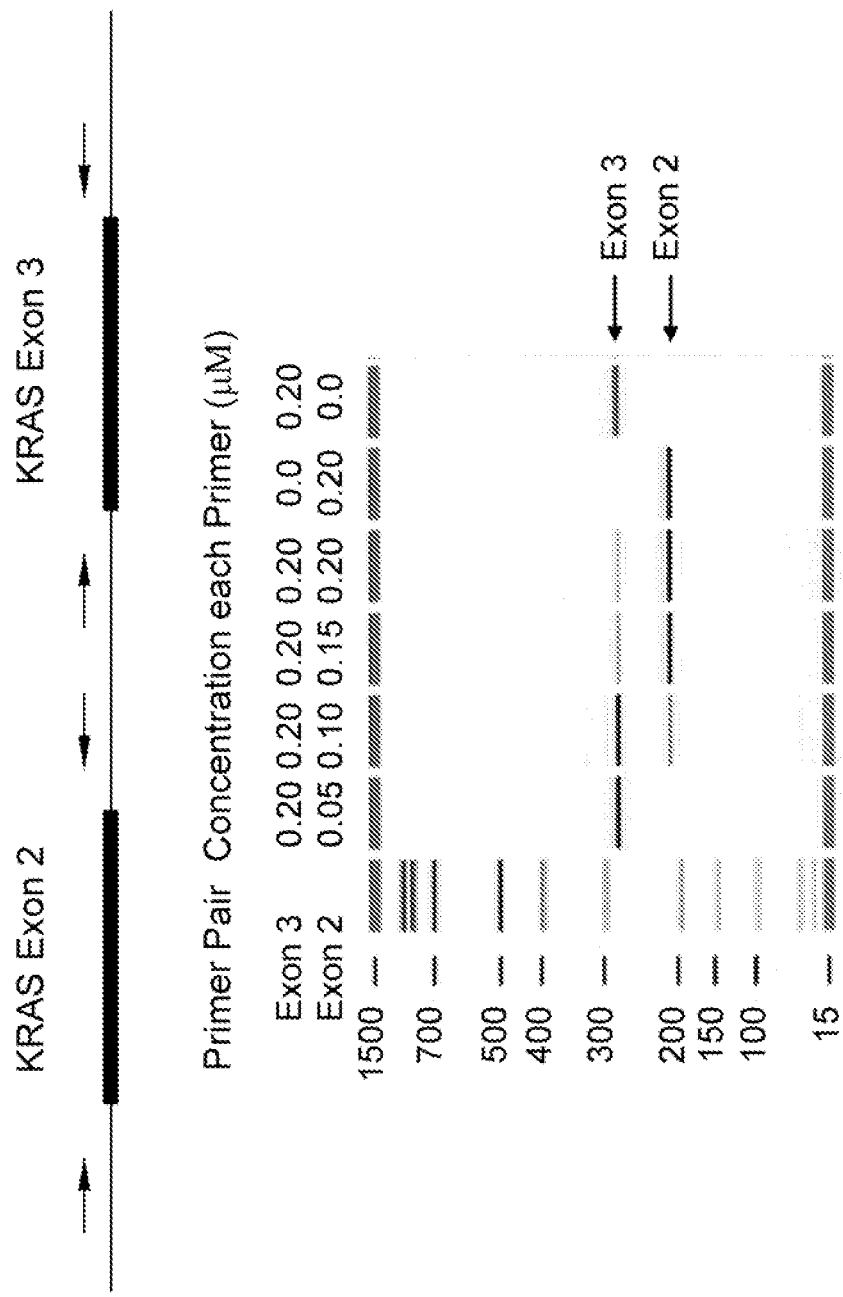
FIG. 7 illustrates the effect of varying the concentration of the PCR primer sets on the amplification of DNA fragments for KRAS exons 2 and 3. The ability to amplify DNA fragments was dependent on the ratio of the PCR primer sets to each other. Increasing the concentration of one set of primers, relative to a second set, favors amplification of the first product over the second. After the adjustment of the primer set concentrations, this experiment was repeated with modified PCR primers until all PCR products were amplified to similar amounts as judged by gel analysis.

FIG. 7 is an example of the multiplex PCR amplification of KRAS exons 2 and 3, where equal concentrations of primers and gDNA template resulted in varying degrees of amplification of these PCR templates. Applicants found that when more than two PCR primer sets or primers/probes are used, changing one primer concentration will more probably than not result in changes in all PCR products or SNPE products (data not shown). Similar results were observed when more than 10 SNPE primers/probes were used to interrogate large number of mutation hotspots. Without wishing to be bound by any theory, Applicants believe that strong competition between primer pairs makes adjustment of relative peak heights difficult, in that changing the concentration of one primer will result in the re-equilibration of many other primers/probes.

TABLE 1

| Gene | Region | Sequence (5' to 3') | Tm (° C.) | Final Concentration (nM) |
|---|---|---|---|---|
| KRAS Pool | exon 2, forward | TGTGACATGTTCTAATATAGTCA CATT (SEQ ID NO: 1) | 59.32 | 500 |
|  | exon 2, reverse | CACAAAATGATTCTGAATTAGC T (SEQ ID NO: 2) | 58.8 | 500 |

TABLE 1-continued

| Gene | Region | Sequence (5' to 3') | Tm (° C.) | Final Concentration (nM) |
|---|---|---|---|---|
| | exon 3, forward | GGAAGCAAGTAGTAATTGATGG (SEQ ID NO: 3) | 59.14 | 200 |
| | exon 3, reverse | AAAGAAAGCCCTCCCC (SEQ ID NO: 4) | 59.07 | 200 |
| | exon 4, forward | GAACAGTAGACACAAAACAGG C (SEQ ID NO: 5) | 60.23 | 200 |
| | exon 4, reverse | TGCAGAAAACAGATCTGTATTT ATTT (SEQ ID NO: 6) | 60.73 | 200 |
| NRAS Pool | exon 2, forward | GGTGTGAAATGACTGAGTAC (SEQ ID NO: 7) | 54.21 | 100 |
| | exon 2, reverse | GGGCCTCACCTCTATGGTG (SEQ ID NO: 8) | 64.49 | 100 |
| | exon 3, forward | GGTGAAACCTGTTTGTTGGA (SEQ ID NO: 9) | 62.38 | 150 |
| | exon 3, reverse | ATACACAGAGGAAGCCTTCG (SEQ ID NO: 10) | 60.82 | 150 |
| BRAF Pool | Exon 15, forward | TCTTCATGAAGACCTCACAGT (SEQ ID NO: 11) | 58.85 | 100 |
| | Exon 15, reverse | CCAGACAACTGTTCAAACTGA (SEQ ID NO: 12) | 60.35 | 100 |
| | exon 11, forward | GTGATGATTGGGAGATTCCT (SEQ ID NO: 13) | 60.3 | 150 |
| | exon 11, reverse | CTGCCACATCACCATGCCA (SEQ ID NO: 14) | 69.62 | 150 |

Probes for the SNPE reaction (Table 2) (SEQ ID NOS: 15-42) were chosen by selecting regions of genes immediately adjacent 3' to the base of interest. Both sense and antisense strands were used in designing the SNPE probes. Size based resolution of the probes was made possible by the addition of GATC repeats or poly T tails (GATC, T10 up to T49 in Table 2) on the 5' end of the probe. In one instance a mixed poly T-C oligo tail (T10 C10 T36) was used.

The detection of the BRAF double mutations, V600K and V600R, presented special challenges in SNPE probe design. In addition to designing oligonucleotide primers/probes from both the sense and anti-sense directions, Applicants designed additional primers/probes directed to all of the potential mutations at these positions (Table 6). As shown in Table 2, the BRAF-2 pool included the primer/probe 1799 (A)/600 which detected any mutant with an A at the 1799 nucleotide position, including the double mutation such as V600R (GTG to AGG). This design was also needed to detect the more aggressive BRAF double mutation, V600K, which has reported as a possible link to the tumor metastasis (Menzies, A. M., et al., *Clin. Cancer Res.*, 2012, 18(12): 3242-3249; Rosalyn, J., et al., *Clin. Cancer Res.*, 2012, 18(24):6792).

TABLE 2

| Reaction | Region | Sequence (5' to 3') | Size (nt) | Strand Probed | Tm (° C.)* | Final Conc. (nM) |
|---|---|---|---|---|---|---|
| KRAS | 34/12 | AACTTGTGGTAGTTGGAGCT (SEQ ID NO: 15) | 20 | sense | 57.84 | 25 |
| | 35/12 | GATCGTACTTGTGGTAGTTGG AGCTG (SEQ ID NO: 16) | 26 | sense | 60.24 | 75 |
| | 37/13 | GATCGATCGATCTTGTGGTAG TTGGAGCTGGT (SEQ ID NO: 17) | 32 | sense | 62.15 | 25 |
| | 38/13 | GATCGATCGATCGATCGATGT GGTAGTTGGAGCTGGTG (SEQ ID NO: 18) | 38 | sense | 65.61 | 75 |
| | 181/61 | TTTTTTTTTTTTTTTTTTTTT TTTTTCTCATTGCACTGTACTCC TCTT (SEQ ID NO: 19) | 50 | antisense | 59.95 | 25 |

TABLE 2-continued

| Reaction | Region | Sequence (5' to 3') | Size (nt) | Strand Probed | Tm (° C.)* | Final Conc. (nM) |
|---|---|---|---|---|---|---|
| | 182/ 61 | TTTTTTTTTTTTTTTTTTTT TTTTTTTTTTTTATTCTCGACAC AGCAGGTC (SEQ ID NO: 20) | 54 | sense | 60.45 | 25 |
| | 183/ 61 | TTTTTTTTTTTTTTTTTTTT TTTTTTTTTTTTTTTTCCTC ATTGCACTGTACTCCTC (SEQ ID NO: 21) | 63 | antisense | 61.29 | 65 |
| | 436/ 146 | TTTTTTTTTTTTTTTTTTTT TTTTTTTTTTTTTTTTTTTT TTTGTCTTACTTAGCTGTCTTGT CTTTG (SEQ ID NO: 22) | 73 | sense | 59.23 | 400 |
| | 437/ 146 | TTTTTTTTTTCCCCCCCCCCTTT TTTTTTTTTTTTTTTTTTT TTTTTTTTTGAATTCCTTTTAT TGAAACATCAG (SEQ ID NO: 23) | 81 | antisense | 59.41 | 400 |
| NRAS | 35/ 12 | TTTTTTTTTTTTTTTTTTTTC TGGTGGTGGTTGGAGCAG (SEQ ID NO: 24) | 41 | sense | 66.93 | 75 |
| | 37/ 13 | TTTTTTTTTTTTTTTTTTTT TTTTTGGTGGTGGTTGGAGCA GGT (SEQ ID NO: 25) | 47 | sense | 67.46 | 3 |
| | 38/ 13 | TTTTTTTTTTTTTTTTTTTT TTTTTTTTGTCAGTGCGCTTTT CCCAACA (SEQ ID NO: 26) | 53 | antisense | 69.39 | 125 |
| | 181/ 61 | TTTTTTTTTTTTTTTTTTTT TTTTTTTTTTTTCTCATGGCA CTGTACTCTTCTT (SEQ ID NO: 27) | 59 | antisense | 59.95 | 263 |
| | 182/ 61 | TTTTTTTTTTTTTTTTTTTT TTTTTTTTTTTTTTTTTGAC ATACTGGATACAGCTGGAC (SEQ ID NO: 28) | 65 | sense | 60.04 | 35 |
| | 183/ 61 | TTTTTTTTTTTTTTTTTTTT TTTTTTTTTTTTTTTTTTTT TTTCTCTCATGGCACTGTACTCT TC (SEQ ID NO: 29) | 71 | antisense | 60.48 | 70 |
| BRAF-1 | 1774/ 592 | TTTTTTTTTTTTTTTCATGAA GACCTCACAGTAAAA (SEQ ID NO: 30) | 36 | sense | 56.8 | 250 |
| | 1781/ 594 | TTTTTTTTTTTTTTTTTTTTA CCTCACAGTAAAAATAGGTG (SEQ ID NO: 31) | 42 | sense | 54.84 | 250 |
| | 1782/ 594 | TTTTTTTTTTTTTTTTTTTTT TTTGATTTCACTGTAGCTAGAC CAAA (SEQ ID NO: 32) | 48 | antisense | 58.94 | 125 |
| | 1786/ 596 | TTTTTTTTTTTTTTTTTTTT TTTTTTTTTTGAGATTTCACT GTAGCTAGAC (SEQ ID NO: 33) | 54 | antisense | 52.16 | 250 |
| | 1789/ 597 | TTTTTTTTTTTTTTTTTTTT TTTTTTTTTTTTTTGTAAA AATAGGTGATTTTGGT (SEQ ID NO: 34) | 60 | sense | 53.91 | 250 |
| | 1790/ 597 | TTTTTTTTTTTTTTTTTTTT TTTTTTTTTTTTTTTTTTTT TCATCGAGATTTCACTGTAGCT (SEQ ID NO: 35) | 66 | antisense | 58.52 | 250 |

TABLE 2-continued

| Reaction | Region | Sequence (5' to 3') | Size (nt) | Strand Probed | Tm (° C.)* | Final Conc. (nM) |
|---|---|---|---|---|---|---|
| BRAF-2 | 1799 (A)/ 600 | TTTTTTTTTTTTGGTGATTT TGGTCTAGCTACAA (SEQ ID NO: 36) | 35 | sense | 59.65 | 62 |
| | 1799 (G)/ 600 | TTTTTTTTTTTTTTTTTGGT GATTTGGTCTAGCTACAG (SEQ ID NO: 37) | 41 | sense | 59.29 | 62 |
| | 1800/ 600 | TTTTTTTTTTTTTTTTTTTT TTTTGGACCCACTCCATCGAGA TTT (SEQ ID NO: 38) | 47 | antisense | 66.21 | 62 |
| | 1798/ 600 | TTTTTTTTTTTTTTTTTTTT TTTTTTTTTGGTGATTTTGGT CTAGCTACA (SEQ ID NO: 39) | 53 | sense | 58.28 | 31 |
| | 1801/ 601 | TTTTTTTTTTTTTTTTTTTT TTTTTTTTTTTTTTTGGACC CACTCCATCGAGATT (SEQ ID NO: 40) | 59 | antisense | 65.16 | 62 |
| | 2/ 466 | TTTTTTTTTTTTTTTTTTTT TTTTTTTTTTTTTTTTTTTT TGGGACAAAGAATTGGATCTG (SEQ ID NO: 41) | 65 | sense | 60.87 | 62 |
| | 3/ 466 | TTTTTTTTTTTTTTTTTTTT TTTTTTTTTTTTTTTTTTTT TTTTCCTTGTAGACTGTTCCA AATGA (SEQ ID NO: 42) | 71 | antisense | 60.55 | 93 |

*Poly T tails or GATC repeats were omitted for Tm calculations

Example 3

Synthetic Oligonucleotides as Templates for the SNPE Assay

Because of the difficulty in obtaining cell lines with all of the specific mutations of interest, Applicants employed synthetic oligonucleotide templates, containing wild-type and mutant sequences in both sense and anti-sense directions, to validate the SNPE primers/probes for their specificity in detecting each mutation of interest. The oligonucleotide templates are synthetic, single-stranded DNA that mimics the respective PCR products. As such, there was no substantial difference between the use of the synthetic templates and the PCR products obtained from cell lines with the specific mutations.

Figure 8:
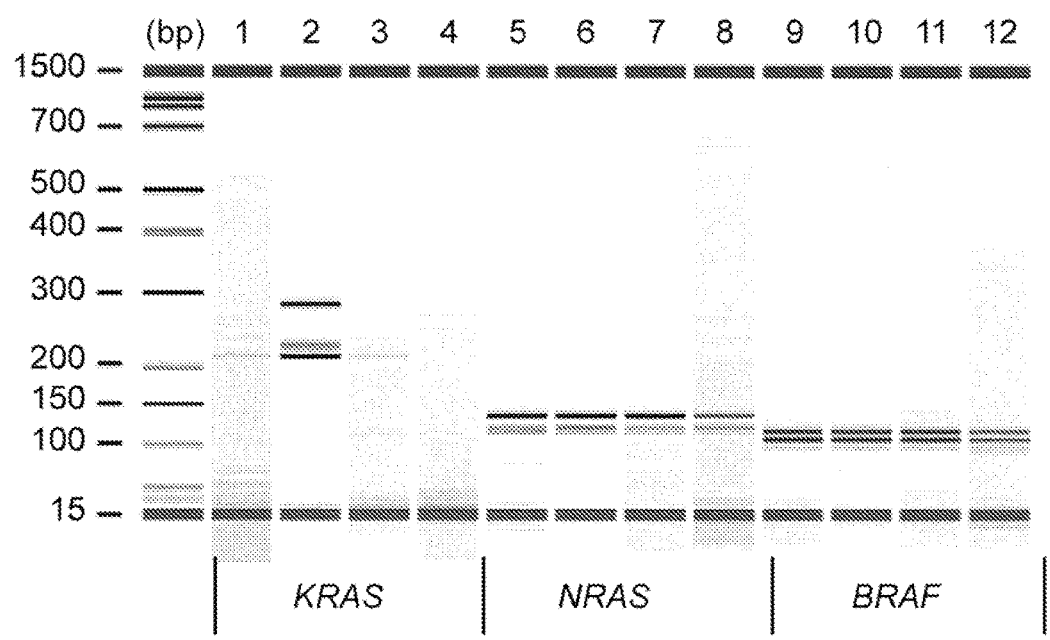
FIG. 8 illustrates the inability to amplify large DNA fragments (amplicons) from formalin-fixed paraffin embedded (FFPE) derived genomic DNA (gDNA) by polymerase chain reaction (PCR). Replicate samples of FFPE gDNA from four tumor types (ovarian cancer: lanes 1, 5, and 9; lung cancer: lanes 2, 6, and 10; colorectal cancer: lanes 3, 7, and 11; pancreatic cancer: lanes 4, 8, and 12) were subjected to PCR amplification for KRAS, NRAS, and BRAF exons. PCR primers for KRAS were designed to amplify fragments of DNA 200-300 bp in size, while PCR primers for NRAS and BRAF were designed to amplify fragments 125-150 bp in size. Three out of four PCR reactions for KRAS failed to successfully amplify DNA fragments while all PCR reactions of NRAS and BRAF were successful.
Figure 9:
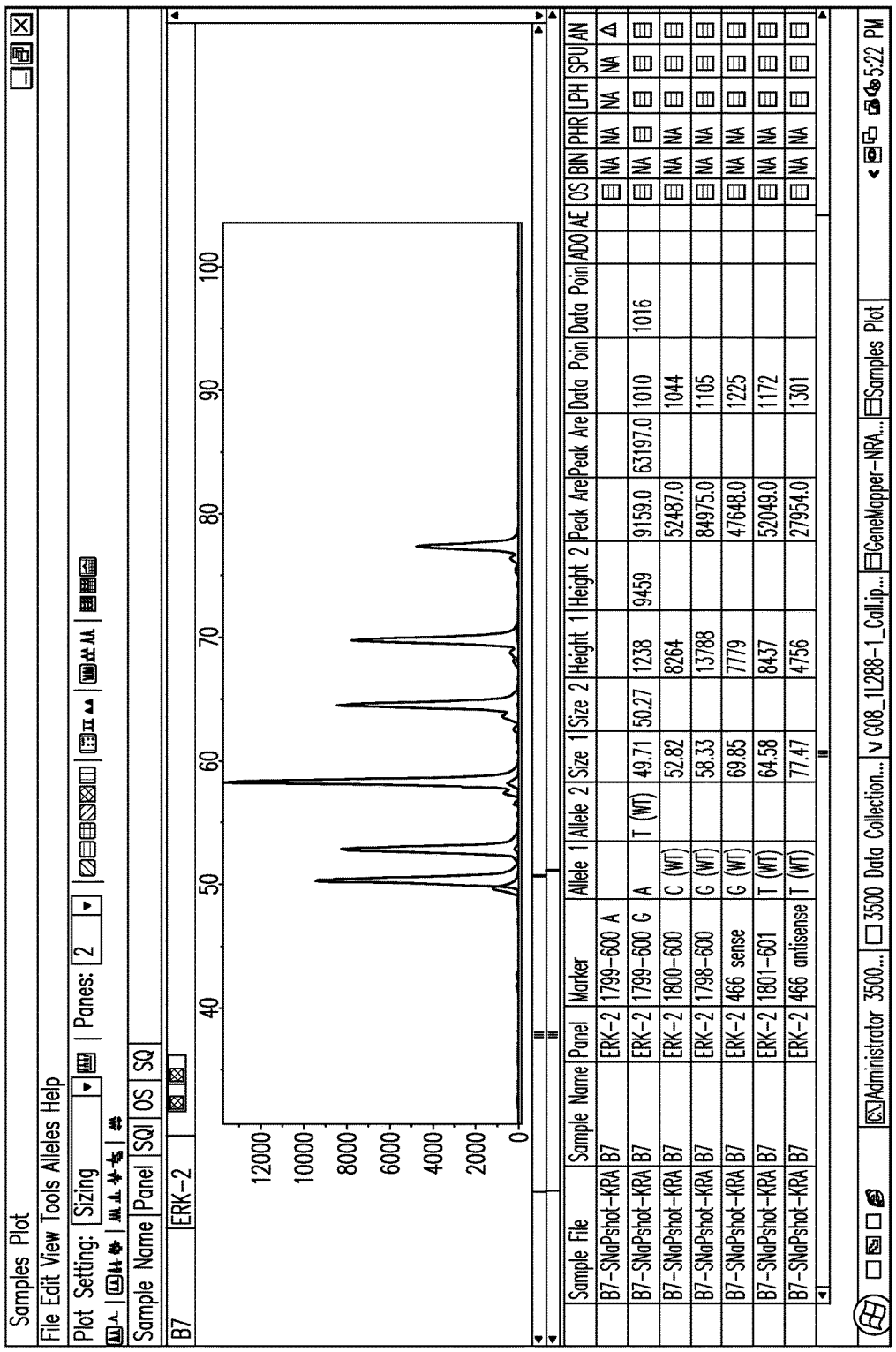
FIG. 9 is an example of a data output for the BRAF probe 1799 (G)/600 (Table 2) with the variant caller, Gene Mapper (Applied Biosystems, Foster City, Calif.), for wild-type and mutants in a tabular format. The output shows that Alelle 1 had the mutation corresponding to V600E (Table 5).

Applicants found that the size of the amplicon, i.e., the PCR products generated from two PCR primers through PCR cycles, used for the PCR template was critical to successfully detect the mutations with FFPE tissue samples using the KBN-SNPE assay. Initial design efforts and assay optimization were conducted using normal human blood gDNA samples. While data generated using longer PCR templates containing the mutation hotspots was successful, when FFPE tumor tissue samples were used, amplification of the target regions was inconsistent (FIG. 8), presumably because the DNA from FFPE tissue samples was highly fragmented and/or degraded. Applicants shortened the length of the amplicons used herein to accommodate the low quality sample common with FFPE tissue.

Synthetic oligonucleotides (Table 3) (SEQ ID NOS: 43-100), made up as 100 μM stock in distilled water, were diluted 1:200 in 1× calf intestine alkaline phosphatase (CIP) (New England BioLabs, Ipswich, Mass.) buffer. 15 μL of diluted stock was transferred to a microtiter plate and treated with 5 units CIP at 37° C. for 60 minutes, followed by 70° C. for 15 minutes. One microliter of the CIP treated oligonucleotide was mixed with 9 μL SNPE reaction mixture. The remaining incubation and analysis methods were the same as that described for gDNA (Example 2).

TABLE 3

| Gene | Codon Number | Codon | Protein Description | Sequence |
|---|---|---|---|---|
| BRAF | 466 | GGA | G466G | TACAGTGGGACAAAGAATTGGATCTGGATCATTTG GAACAGTCTACAAGGGAA (SEQ ID NO: 43) |
| | 466 | GGA | G466G | TTCCCTTGTAGACTGTTCCAAATGATCCAGATCCA ATTCTTTGTCCCACTGTA (SEQ ID NO: 44) |
| | 466 | GAA | G466E | TTCCCTTGTAGACTGTTCCAAATGATTCAGATCCA ATTCTTTGTCCCACTGTA (SEQ ID NO: 45) |

TABLE 3-continued

| Gene | Codon Number | Codon | Protein Description | Sequence |
|---|---|---|---|---|
| | 466 | GTA | G466V | TACAGTGGGACAAAGAATTGGATCTGTATCATTTG GAACAGTCTACAAGGGAA (SEQ ID NO: 46) |
| | 592 | ATA | I592I | TCACTGTAGCTAGACCAAAATCACCTATTTTTACT GTGAGGTCTTCATGAAGA (SEQ ID NO: 47) |
| | 592 | GTA | I592V | TCACTGTAGCTAGACCAAAATCACCTAGTTTTACT GTGAGGTCTTCATGAAGA (SEQ ID NO: 48) |
| | 594 | GAT | D594D | TGAAGACCTCACAGTAAAAATAGGTGATTTTGGTC TAGCTACAGTGAAATCTC (SEQ ID NO: 49) |
| | 594 | GAT | D594D | GAGATTTCACTGTAGCTAGACCAAAATCACCTATT TTTACTGTGAGGTCTTCA (SEQ ID NO: 50) |
| | 594 | GTT | D594V | GAGATTTCACTGTAGCTAGACCAAAACACCTATT TTTACTGTGAGGTCTTCA (SEQ ID NO: 51) |
| | 594 | GAA | D594E | TGAAGACCTCACAGTAAAAATAGGTGAATTTGGT CTAGCTACAGTGAAATCTC (SEQ ID NO: 52) |
| | 594 | GAG | D594E | TGAAGACCTCACAGTAAAAATAGGTGAGTTTGGT CTAGCTACAGTGAAATCTC (SEQ ID NO: 53) |
| | 596 | GGT | G596G | CCTCACAGTAAAAATAGGTGATTTGGTCTAGCTA CAGTGAAATCTCGATGGA (SEQ ID NO: 54) |
| | 596 | GGT | G596G | TCCATCGAGATTTCACTGTAGCTAGACCAAAATCA CCTATTTTTACTGTGAGG (SEQ ID NO: 55) |
| | 596 | CGT | G596R | CCTCACAGTAAAAATAGGTGATTTTCGTCTAGCTA CAGTGAAATCTCGATGGA (SEQ ID NO: 56) |
| | 597 | TCA | L597S | CCTCACAGTAAAAATAGGTGATTTTCGTTCAGCTA CAGTGAAATCTCGATGGA (SEQ ID NO: 57) |
| | 597 | TCA | L597S | TCCATCGAGATTTCACTGTAGCTGAACGAAAATCA CCTATTTTTACTGTGAGG (SEQ ID NO: 58) |
| | 600 | GTG | V600V | AATAGGTGATTTTGGTCTAGCTACAGTGAAATCTC GATGGAGTGGGTCCCATC (SEQ ID NO: 59) |
| | 600 | GTG | V600V | GATGGGACCCACTCCATCGAGATTTCACTGTAGCT AGACCAAAATCACCTATT (SEQ ID NO: 60) |
| | 600 | GAG | V600E | GATGGGACCCACTCCATCGAGATTTCTCTGTAGCT AGACCAAAATCACCTATT (SEQ ID NO: 61) |
| | 600 | AGG | V600R | GATGGGACCCACTCCATCGAGATTTCCTTGTAGCT AGACCAAAATCACCTATT (SEQ ID NO: 62) |
| | 600 | AAG | V600K | GATGGGACCCACTCCATCGAGATTTCTTTGTAGCT AGACCAAAATCACCTATT (SEQ ID NO: 63) |
| | 600 | GAT | V600D | AATAGGTGATTTTGGTCTAGCTACAGATAAATCTC GATGGAGTGGGTCCCATC (SEQ ID NO: 64) |
| | 600 | GAT | V600D | GATGGGACCCACTCCATCGAGATTTATCTGTAGCT AGACCAAAATCACCTATT (SEQ ID NO: 65) |
| | 601 | GAA | K601E | AGGTGATTTTGGTCTAGCTACAGTGGAATCTCGAT GGAGTGGGTCCCATCAGT (SEQ ID NO: 66) |
| KRAS | 12 | GGT | G12G | GTATCGTCAAGGCACTCTTGCCTACGCCACCAGCT CCAACTACCACAAGTTTA (SEQ ID NO: 67) |
| | 12 | AGT | G12S | GTATCGTCAAGGCACTCTTGCCTACGCCACTAGCT CCAACTACCACAAGTTTA (SEQ ID NO: 68) |
| | 12 | TGT | G12C | GTATCGTCAAGGCACTCTTGCCTACGCCACAAGCT CCAACTACCACAAGTTTA (SEQ ID NO: 69) |
| | 12 | GAT | G12D | GTATCGTCAAGGCACTCTTGCCTACGCCATCAGCT CCAACTACCACAAGTTTA (SEQ ID NO: 70) |

TABLE 3-continued

| Gene | Codon Number | Codon | Protein Description | Sequence |
|---|---|---|---|---|
| | 12 | GCT | G12A | GTATCGTCAAGGCACTCTTGCCTACGCCAGCAGCT CCAACTACCACAAGTTTA (SEQ ID NO: 71) |
| | 12 | GTT | G12V | GTATCGTCAAGGCACTCTTGCCTACGCCAACAGCT CCAACTACCACAAGTTTA (SEQ ID NO: 72) |
| | 13 | GGC | G13G | GTATCGTCAAGGCACTCTTGCCTACGCCACCAGCT CCAACTACCACAAGTTTA (SEQ ID NO: 73) |
| | 13 | CGC | G13R | GTATCGTCAAGGCACTCTTGCCTACGCGACCAGCT CCAACTACCACAAGTTTA (SEQ ID NO: 74) |
| | 13 | GAC | G13D | GTATCGTCAAGGCACTCTTGCCTACGTCACCAGCT CCAACTACCACAAGTTTA (SEQ ID NO: 75) |
| | 61 | CAA | Q61Q | CTTGGATATTCTCGACACAGCAGGTCAAGAGGAG TACAGTGCAATGAGGGACC (SEQ ID NO: 76) |
| | 61 | CAA | Q61Q | GGTCCCTCATTGCACTGTACTCCTCTTGACCTGCTG TGTCGAGAATATCCAAG (SEQ ID NO: 77) |
| | 61 | AAA | Q61K | CTTGGATATTCTCGACACAGCAGGTAAAGAGGAG TACAGTGCAATGAGGGACC (SEQ ID NO: 78) |
| | 61 | CTA | Q61L | GGTCCCTCATTGCACTGTACTCCTCTTTACCTGCTG TGTCGAGAATATCCAAG (SEQ ID NO: 79) |
| | 61 | CAC | Q61H | CTTGGATATTCTCGACACAGCAGGTCACGAGGAGT ACAGTGCAATGAGGGACC (SEQ ID NO: 80) |
| | 61 | CAT | Q61H | CTTGGATATTCTCGACACAGCAGGTCATGAGGAGT ACAGTGCAATGAGGGACC (SEQ ID NO: 81) |
| | 146 | GCA | A146A | TGGAATTCCTTTTATTGAAACATCAGCAAAGACAA GACAGGTAAGTAACACTG (SEQ ID NO: 82) |
| | 146 | GCA | A146A | CAGTGTTACTTACCTGTCTTGTCTTTGCTGATGTTT CAATAAAAGGAATTCCA (SEQ ID NO: 83) |
| | 146 | ACA | A146T | CAGTGTTACTTACCTGTCTTGTCTTTGTTGATGTTT CAATAAAAGGAATTCCA (SEQ ID NO: 84) |
| | 146 | ACA | A146T | TGGAATTCCTTTTATTGAAACATCAACAAAGACAA GACAGGTAAGTAACACTG (SEQ ID NO: 85) |
| | 146 | GTA | A146V | TGGAATTCCTTTTATTGAAACATCAGTAAAGACAA GACAGGTAAGTAACACTG (SEQ ID NO: 86) |
| | 146 | GTA | A146V | CAGTGTTACTTACCTGTCTTGTCTTTACTGATGTTT CAATAAAAGGAATTCCA (SEQ ID NO: 87) |
| NRAS | 12 | GGT | G12G | CAAACTGGTGGTGGTTGGAGCAGGTGGTGTTGGG AAAAGCGCACTGACAATCC (SEQ ID NO: 88) |
| | 12 | GGT | G12G | GGATTGTCAGTGCGCTTTTCCCAACACCACCTGCT CCAACCACCACCAGTTTG (SEQ ID NO: 89) |
| | 12 | GAT | G12D | CAAACTGGTGGTGGTTGGAGCAGATGGTGTTGGG AAAAGCGCACTGACAATCC (SEQ ID NO: 90) |
| | 12 | GTT | G12V | CAAACTGGTGGTGGTTGGAGCAGTTGGTGTTGGG AAAAGCGCACTGACAATCC (SEQ ID NO: 91) |
| | 13 | GAT | G13D | CAAACTGGTGGTGGTTGGAGCAGGTGATGTTGGG AAAAGCGCACTGACAATCC (SEQ ID NO: 92) |
| | 13 | CGT | G13R | GGATTGTCAGTGCGCTTTTCCCAACACGACCTGCT CCAACCACCACCAGTTTG (SEQ ID NO: 93) |
| | 61 | CAA | Q61Q | GTTGGACATACTGGATACAGCTGGACAAGAAGAG TACAGTGCCATGAGAGACC (SEQ ID NO: 94) |
| | 61 | CAA | Q61Q | GGTCTCTCATGGCACTGTACTCTTCTTGTCCAGCTG TATCCAGTATGTCCAAC (SEQ ID NO: 95) |

TABLE 3-continued

| Gene | Codon Number | Codon | Protein Description | Sequence |
|---|---|---|---|---|
| | 61 | AAA | Q61K | GTTGGACATACTGGATACAGCTGGAAAAGAAGAG TACAGTGCCATGAGAGACC (SEQ ID NO: 96) |
| | 61 | CGA | Q61R | GGTCTCTCATGGCACTGTACTCTTCTCGTCCAGCT GTATCCAGTATGTCCAAC (SEQ ID NO: 97) |
| | 61 | CTA | Q61L | GGTCTCTCATGGCACTGTACTCTTCTAGTCCAGCT GTATCCAGTATGTCCAAC (SEQ ID NO: 98) |
| | 61 | CAC | Q61H | GTTGGACATACTGGATACAGCTGGACACGAAGAG TACAGTGCCATGAGAGACC (SEQ ID NO: 99) |
| | 61 | CAT | Q61H | GTTGGACATACTGGATACAGCTGGACATGAAGAG TACAGTGCCATGAGAGACC (SEQ ID NO: 100) |

Example 4

Single Nucleotide Primer Extension (SNPE) Assay

Figure 5A:
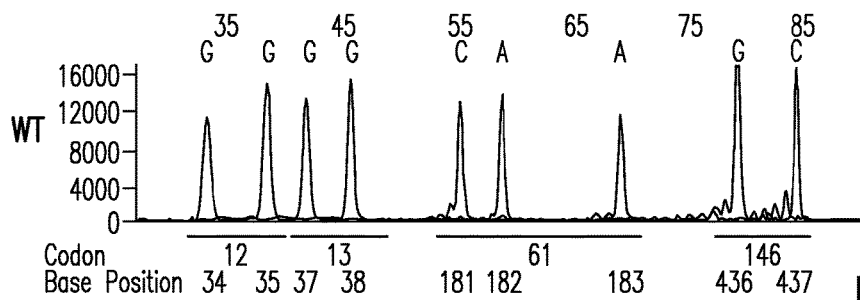
FIGS. 5A-5E are graphics illustrating the ERK Mutation Assay results for the KRAS Probe Pool: (wild type (WT) control (FIG. 5A); G12S mutation (MT) (FIG. 5B); G12D mutation (MT) (FIG. 5C); G12V mutation (MT) (FIG. 5D); and the G13D mutation (MT) (FIG. 5E). The position of the codons and nucleotides are indicated at the bottom of the figure. The nucleotide label for each peak has been converted to the sense strand.
Figure 5B:
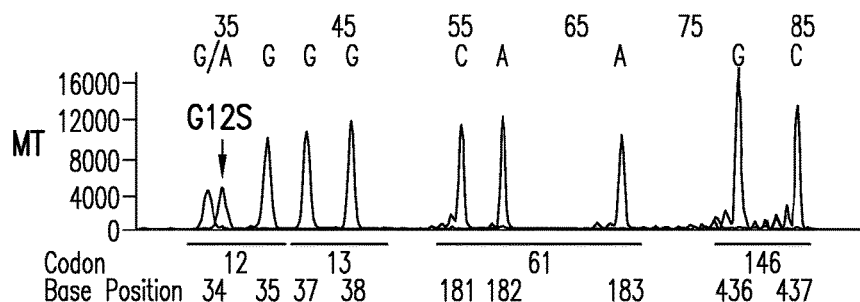
Figure 5C:
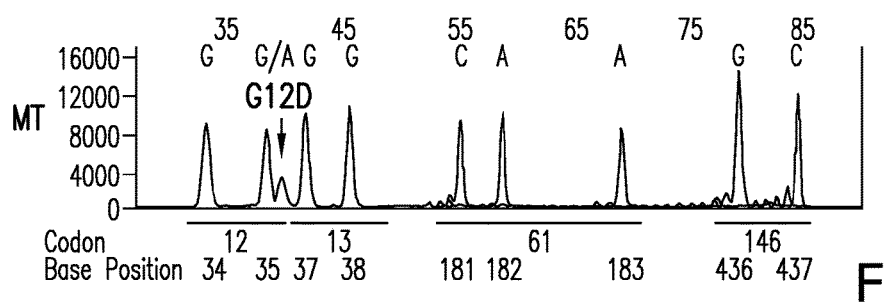
Figure 5D:
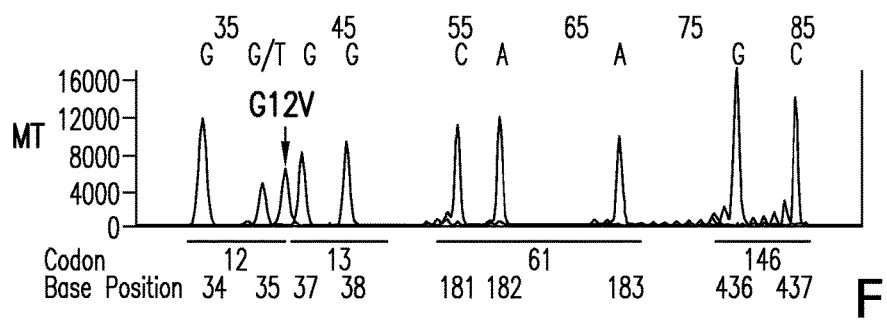
Figure 5E:
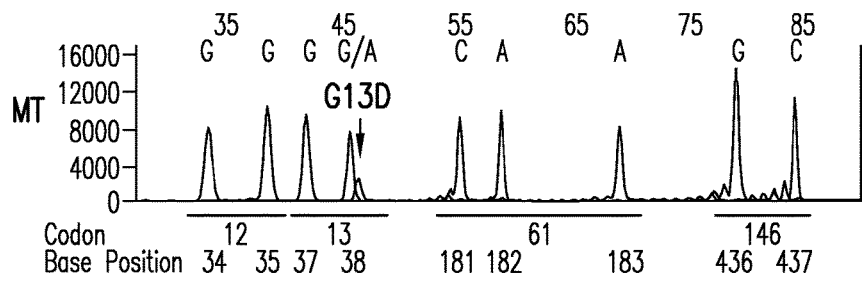

Fifteen (15) ng of isolated gDNA was used as a template for PCR amplification of KRAS exons 2, 3 and 4 (FIG. 5A), NRAS exons 2 and 3 (FIG. 5C) and BRAF exons 11 and 15 (FIG. 5B). Each gene was independently amplified by PCR. For each PCR reaction 25 μL ABI AmpliTaq Gold Master Mix (ABI cat #4398886), 5 μL PCR primer pool (Table 2S), 3 μL gDNA (5 ng/μL), and 17 μL distilled water were mixed and subjected to 40 rounds of PCR amplification. The PCR conditions were as follows: 96° C., 5 minutes, 40 cycles of amplification, wherein each cycle consists of 94° C., 30 seconds, 55° C., 55 seconds, 72° C., 45 seconds. After 40 cycles the reactions were incubated at 72° C. for 10 minutes then held at 4° C. until processed in the single nucleotide primer extension (SNPE) assay. Any remaining PCR product was stored at −20° C.

Prior to using the PCR product as a template in the single SNPE assay, 15 μL of each PCR product was treated with 5 units of calf intestine alkaline phosphatase (CIP) (New England BioLabs, Ipswich, Mass.) and 2 units of Exonuclease I (ExoI, Affymetrix/USB, Cleveland, Ohio) at 37° C., 1 hour, followed by 70° C., 0.25 hour in a final volume of 16 μl. 3 μL of the CIP/Exo I treated PCR product was then used in the SNPE assay without further adjustment to the DNA concentration. Each single nucleotide primer extension reaction consisted of 5 μL SNaPshot Multiplex Kit (Applied Biosystems, Life Technologies, Carlsbad, Calif.), 3 μL CIP/ExoI treated PCR product, 1 μL SNPE probe pool (see, Table 2 for probe sequence and concentrations used), and 1 μL water. The SNPE reaction cycling conditions were as follows: 96° C., 10 seconds, 50° C., 5 seconds, 60° C., 30 seconds, for 25 cycles. Samples were maintained at 4° C. until analyzed. For analysis, each SNPE reaction was treated with 1 unit CIP, 37° C., for 1 hour followed by 70° C., for 0.25 hour. One-half microliter (0.5 μL) of the CIP treated single SNPE reaction product was mixed with 0.5 μL GeneScan 120 LIZ size standards (Applied Biosystems, Life Technologies, Carlsbad, Calif.) and 9.0 uL Hi-Di Formamide (Applied Biosystems, Life Technologies, Carlsbad, Calif.), denatured at 95° C. for 5 minutes. After denaturing, the samples were immediately placed on ice for 5 minutes then centrifuged and loaded onto an ABI 3500 Genetic analyzer (Applied Biosystems, Life Technologies, Carlsbad, Calif.) equipped with a 50 cm capillary using POP 7 polymer (Applied Biosystems, Life Technologies, Carlsbad, Calif.). Results of the capillary electrophoresis run were imported into ABI GeneMapper (version 4.1) (Applied Biosystems, Life Technologies, Carlsbad, Calif.) where pre-programmed base calling functions for KRAS, BRAF and NRAS identified the bases found at each position examined.

Example 5

Assaying Samples in Triplicate

In experiments where samples were assayed in triplicate, the rules for determining the consensus call are presented in Table 4. If the same call was determined in two of three or three of three reactions, then the majority call was the consensus. Where a call was not possible (ND) in two or more replicates, the consensus call was considered to be indeterminate. When performed in support of a clinical trial, re-do rules would be applied and samples where clear results could not be obtained would be re-assayed. Two failed attempts would result in a "No-Call" result and a new sample would be requested.

TABLE 4

| Replicate/Call | | | |
|---|---|---|---|
| 1 | 2 | 3 | Consensus |
| Wild Type | Wild Type | Wild Type | Wild Type |
| Wild Type | Wild Type | Mutation-1 | Wild Type |
| Wild Type | Mutation-1 | Mutation-1 | Mutation-1 |
| Mutation-1 | Mutation-1 | Mutation-1 | Mutation-1 |
| Wild Type | Wild Type | ND* | Wild Type |
| Mutation-1 | Mutation-1 | ND | Mutation-1 |
| Wild Type | ND | ND | Indeterminate-Redo |
| ND | ND | ND | Indeterminate-Redo |
| Mutation-1 | ND | ND | Indeterminate-Redo |
| Wild Type | Mutation-1 | ND | Indeterminate-Redo |
| Mutation-1 | Mutation-1 | Mutation-2 | Mutation-1 |
| Mutation-1 | Wild Type | ND | Indeterminate-Redo |

*ND = Not Determined

Example 6

Sanger Sequencing

Sanger sequencing, often referred to as "First Generation" sequencing, was accomplished using ABI BigDye Direct Cycle Sequencing Kit (ABI #4458687) (Applied Biosystems, Life Technologies, Carlsbad, Calif.) with M13 modified PCR primers and following the manufacturer's instructions. The reaction mixture was applied to an ABI 3500

Genetic analyzer (Applied Biosystems, Life Technologies, Carlsbad, Calif.) equipped with a 50 cm capillary using POP 7 polymer.

Example 7

Ion Semiconductor Sequencing 80 ng of gDNA from discordant samples were analyzed by ion semiconductor sequencing on the Ion PGM sequencer (Life Technologies, Carlsbad, Calif.). Targeted exon enrichment was performed using the GeneRead DNA panel. Enrichment was accomplished using 20-25 PCR cycles. Library construction was made using Life Tech's Ion Xpres Plus gDNA and Amplicon Library construction kit (Life Technologies, Carlsbad, Calif.). Variant calls were made using two algorithms, Ion Torrent Variant Caller (Life Technologies, Carlsbad, Calif.) and GATK (The Genome Analysis Tool Kit, Broad Institute, Boston, Mass.). Only variants identified by both algorithms were reported.

Example 8

Calculation of Specificity, Sensitivity and Concordance

Concordance was determined at the sample (patient) level. Each sample was subjected to mutation analysis by the SNPE assay (ERK Mutation Assay) and Sanger sequencing as described in Examples 4 (12) and 6, respectively. If the two methods agree, the mutation was assumed to be "truth." If only one method detected a mutation, the sample was analyzed by Ion PGM sequencing (Life Technologies, Carlsbad, Calif.), a type of Next Generation sequencing (NGS), i.e., a high-throughput sequencing technology that parallels the sequencing process. If the Ion PGM result matches either the SNPE (ERK Mutation) or Sanger result, the matched result was considered "truth" and was considered the consensus call. Performance of the SNPE assay (ERK Mutation Assay) was measured versus this consensus call. Samples where a clear result could not be obtained were not included in the concordance calculations.

Example 9

Specificity or Sample-Level Negative Agreement

The specificity of the ERK Mutation Assay is a measure of its ability to identify samples that are wild type for KRAS, BRAF and NRAS. A wild type result in a test with high specificity indicates a high probability of the mutation being absent. Specificity is defined as follows:

Truth: the consensus result obtained by two or more assay methods (ERK Mutation Assay, Sanger sequencing, NGS)
True Positive=sample correctly identified as having a mutation
False Positive=sample incorrectly identified as having a mutation
True Negative=sample correctly identified as not having any mutations (wild type) listed in Table 5
False Negative=sample incorrectly identified as not having any mutation (wild type) listed in Table 5
Specificity=number of True negatives/(number True Negatives+number False Positives)

Table 5 lists the mutations identified by the ERK Mutation Assay and their resulting amino acid change. It should be noted, that while the ERK Mutation Assay was able to detect and identify the known mutations listed in Table 5, because of the degeneracy of the genetic code and the nature of these single nucleotide mutations, the design of the PCR primers (Table 1) (SEQ ID NOS: 1-14) and the SNPE probes (Table 2) (SEQ ID NOS: 15-42) of the inventive assay would enable them to detect and identify additional single nucleotide mutations at the same loci within these genes. Thus, the potential number of single nucleotide polymorphic mutations that can be detected and identified by the inventive assay exceeds those specifically listed in Table 5, estimated to be in excess of 80 mutations.

TABLE 5

| Codon Number | WT Codon | Mutant Codon | Protein Description |
|---|---|---|---|
| BRAF | | | |
| 466 | GGA | GAA | G466E |
| 466 | GGA | GTA | G466V |
| 592 | ATA | GTA | I592V |
| 594 | GAT | GTT | D594V |
| 594 | GAT | GAA | D594E |
| 594 | GAT | GAG | D594E |
| 596 | GGT | CGT | G596R |
| 597 | CTA | TCA | L597S |
| 600 | GTG | GAG | V600E |
| 600 | GTG | AGG | V600R |
| 600 | GTG | AAG | V600K |
| 600 | GTG | GAT | V600D |
| 601 | AAA | GAA | K601E |
| KRAS | | | |
| 12 | GGT | AGT | G12S |
| 12 | GGT | TGT | G12C |
| 12 | GGT | GAT | G12D |
| 12 | GGT | GCT | G12A |
| 12 | GGT | GTT | G12V |
| 13 | GGC | CGC | G13R |
| 13 | GGC | GAC | G13D |
| 61 | CAA | AAA | Q61K |
| 61 | CAA | CTA | Q61L |
| 61 | CAA | CAC | Q61H |
| 61 | CAA | CAT | Q61H |
| 146 | GCA | ACA | A146T |
| 146 | GCA | GTA | A146T |
| NRAS | | | |
| 12 | GGT | GAT | G12D |
| 12 | GGT | GTT | G12V |
| 13 | GGT | CGT | G13R |
| 13 | GGT | GAT | G13D |
| 61 | CAA | AAA | Q61K |
| 61 | CAA | CGA | Q61R |
| 61 | CAA | CTA | Q61L |
| 61 | CAA | CAC | Q61H |

Example 10

Sensitivity or Mutation-Level Positive Agreement

The sensitivity of the KBN-SNPE assay is a measure of its ability to identify samples that contain a mutation listed in Table 5 in KRAS, BRAF, and NRAS. The identification of a mutation present in a highly sensitive assay indicates a high probability of the mutation being present.

Sensitivity or sample level positive agreement is defined as follows:
Sensitivity=number of True Positives/(number of True Positives+number of False Negatives)

Example 11

Overall Concordance

The overall accuracy of the KBN-SNPE assay to make the same wild type or mutation call as the consensus call is defined as follows:

Overall concordance=(number of True Positives+number of True Negatives)/(number of True Positives+number of False Positives+number of False negatives+number of True negatives)

Example 12

ERK Mutation Assay

The SNPE assay (Example 4), which specifically detects ERK Mutations, i.e, mutations to KRAS, BRAF, and NRAS, referred to herein as the ERK Mutation Assay, begins with the PCR amplification of regions of the KRAS, BRAF and NRAS genes from gDNA isolated from one or two 5 µm FFPE slides. A set of probes was hybridized to the amplicons, followed by a single base extension reaction of the probes and capillary electrophoresis separation, and automated base call using the GeneMapper® software (ABI-Life Technologies™, Carlsbad, Calif.) based on size and incorporated fluorescent label. Examples of the output from a ERK Mutation Assay are shown in FIGS. 2-5.

The base called for in each location interrogated is given below each electropherogram (FIGS. 2-5) and indicated whether the nucleotide occupying that position was wild type or mutant. Base calling was determined by the migration of the probe together with the color coding for the nucleotide added during the primer extension reaction. Owing to the slight difference in migration rate, which resulted from the addition of the fluorescently tagged nucleotide of each probe, Applicants identified which of four possible nucleotides was added to the probe.

The ERK Mutation Assay identified the mutations in KRAS, BRAF and NRAS listed in Table 5, which can be used to stratify patients in a clinical trial. The ERK Mutation Assay was designed and validated to perform well with FFPE samples, which generally yield low quality genomic DNA. To work with such samples, Applicants found it necessary to design PCR primers that amplify short stretches (100-150 bp) of DNA (Table 1) (SEQ ID NOS: 1-14) and to carefully balance primer concentrations (FIG. 7) so that all regions were equally amplified.

The ERK Mutation Assay simultaneously interrogates nine and six nucleotide positions within KRAS and NRAS, respectively, and twelve positions within BRAF (Table 2 and FIGS. 6A-6C). KRAS exons 2, 3 and 4, NRAS exons 2 and 3, and BRAF exons 11 and 15 were amplified in three separate PCR reactions (Table 1). These PCR products served as templates for the SNPE reaction used to identify possible mutations. Due to the number of SNPE probes used for BRAF (Table 2) (SEQ ID NOS: 15-42) and sequence similarity between KRAS and NRAS, Applicants found it necessary to perform the primer extension portion of the assay in four separate reactions (Table 2). An additional challenge in the design of this assay was the requirement for the detection of the BRAF V600D (GTG>GAT) mutation in which two adjacent nucleotides are altered. This was accomplished by designing probes to the appropriate regions of the complementary DNA strands (Table 2, FIGS. 6A-6C). In aggregate, Applicants detected 35 specific and 81 potential mutations (counting all possible A/T/G/C changes at each nucleotide location and excluding wild type) at 27 nucleotide positions in the three genes that were dispersed over seven exons. In one embodiment of the invention, the four primer extension reactions are carried out on a single 96 well plate.

Example 13

Analytical Accuracy of the ERK Mutation Assay

To establish the analytical accuracy of the ERK Mutation Assay, three sets of samples from cell lines with previously documented mutations in BRAF or KRAS, synthetic oligonucleotides containing all mutations detected by the KBN-SNPE assay, and a set of sixty formalin-fixed paraffin embedded (FFPE) tumor samples were analyzed by both the KBN-SNPE assay and Sanger sequencing (Example 6)

A. ERK Mutation Assay Detects Known Mutations in Cell Lines

A number of well characterized cell lines with previously defined mutations in KRAS and BRAF are commercially available from ATCC. Such samples mimic tumor samples, but have the advantage that gDNA isolated is free from contamination by gDNA from "normal adjacent" tissue, as would be the case when isolating gDNA from FFPE tumor samples. As such, gDNA isolated from cell lines that are heterozygous for particular mutations represent a pool of gDNA with a "known" percentage of mutant DNA in a wild type background and represent an ideal source of DNA for determining the limits of detection of an assay (see Example 15).

Genomic DNA was isolated from nine cell lines with mutations previously identified by Sanger sequencing as containing mutations in KRAS, BRAF, or NRAS, and two wild type (WT) and compared to the results from the ERK Mutation Assay (Table 6). Of the eleven cell lines examined, ten produced the expected result in the ERK Mutation Assay. The single exception (GAK), which was expected to contain an NRAS mutation, was subjected to re-sequencing by Sanger sequencing and was determined to be wild type for BRAF, KRAS and NRAS, confirming the ERK Mutation result. Without wishing to be bound by any theory, Applicants suggest that the NRAS mutation expected to be present was lost during passage of this cell line.

TABLE 6

| Cell Line (DNA) | Cancer Type | Expected Mutation | KBN-SNPE Mutation |
|---|---|---|---|
| A375 | Melanoma | BRAF, V600E | BRAF, V600E |
| ES-2 | Ovarian | BRAF, V600E | BRAF, V600E |
| WM-266-4 | Melanoma | BRAF, V600D | BRAF, V600D |
| NCI-H358 | Lung | KRAS, G12C | KRAS, G12C |
| HCT-8 | Colon | KRAS, G13D | KRAS, G13D |
| SW 527 | Breast | KRAS, G12V | KRAS, G12V |
| NCI-H2122 | Lung | KRAS, G12C | KRAS, G12C |
| Panc-1 | Pancreatic | KRAS, G12D | KRAS, G12D |
| GAK | Melanoma | NRAS, Q61L | WT* |
| HS-294T | Melanoma | WT | WT |
| ZR-75-1 | Breast | WT | WT |

*Wild type status confirmed by re-sequencing of sample used in the KBN-SNPE assay.

B. ERK Mutation Assay Detects Known Mutations in Synthetic Oligonucleotides

To further establish that the ERK Mutation Assay was able to detect an ERK Mutation, a series of synthetic oligonucleotides (Table 3) (SEQ ID NOS: 43-100) were designed, owing to the limited availability of commercial cell lines containing known mutations, to demonstrate the ERK Mutation Assay's specificity and ability to detect all of the mutations listed in Table 5. These synthetic oligonucleotides replaced the PCR product produced from the genomic DNA in the ERK Mutation Assay. With this exception, the ERK Mutation Assay was performed the same as if genomic DNA was used. All appropriate wild type sequences were included as well. As shown in Table 7, the ERK Mutation Assay accurately identified (Obs'd) all wild type (WT) and mutations (MT) expected (Exp'd) at each position (Position) interrogated.

and 58%, for BRAF and KRAS in the EMA and the COSMIC database, respectively). BRAF mutations in thyroid cancers appear to be over reported (90% in the EMA versus 40% in the COSMIC database). It should also be noted that the rates of mutation reported in the COSMIC database differ from some rates reported in the literature (Downward, J., *Nat. Rev. Cancer,* 2003, 3:11-22; Pearson, G., et al., *Endocr. Rev.,* 2001, 22:153-183; Fecher, L. A., et al., *Curr. Opin. Oncol.,* 2008, 20:183-189; Smalley, K. S. M., *Intl. J. Cancer,* 2003, 104:527-532; Roberts, P. J., and

TABLE 7

| BRAF | | | KRAS | | | NRAS | | |
|---|---|---|---|---|---|---|---|---|
| Position | Exp'd | Obs'd | Position | Exp'd | Obs'd | Position | Exp'd | Obs'd |
| B-G466G-S | WT | WT | K-G12G-AS | WT | WT | N-G12G-S | WT | WT |
| B-G466G-AS | WT | WT | K-G12S-AS | MT | MT | N-G12G-AS | MT | MT |
| B-G466E-AS | MT | MT | K-G12C-AS | MT | MT | N-G12D-S | MT | MT |
| B-G466V-S | MT | MT | K-G12D-AS | MT | MT | N-G12V-S | WT | WT |
| B-I592I-AS | WT | WT | K-G12A-AS | MT | MT | N-G13D-S | MT | MT |
| B-I592V-AS | MT | MT | K-G12V-AS | MT | MT | N-G13R-AS | MT | MT |
| B-D594D-S | WT | WT | K-G13G-AS | WT | WT | N-Q61Q-S | MT | MT |
| B-D594D-AS | WT | WT | K-G13R-AS | MT | MT | N-Q61Q-AS | WT | WT |
| B-D594V-AS | MT | MT | K-G13D-AS | MT | MT | N-Q61K-S | MT | MT |
| B-D594E-S | MT | MT | K-Q61Q-S | WT | WT | N-Q61R-AS | MT | MT |
| B-D594E-S | MT | MT | K-Q61Q-AS | MT | MT | N-Q61L-AS | MT | MT |
| B-G596G-S | WT | WT | K-Q61K-S | MT | MT | N-Q61H-S | MT | MT |
| B-G596G-AS | WT | WT | K-Q61L-AS | MT | MT | N-Q61H-S | MT | MT |
| B-G596R-S | MT | MT | K-Q61H-S | MT | MT | | | |
| B-L597S-S | MT | MT | K-Q61H-S | MT | MT | | | |
| B-L597S-AS | MT | MT | K-A146A-S | WT | WT | | | |
| B-V600V-S | WT | WT | K-A146A-AS | MT | MT | | | |
| B-V600V-AS | WT | WT | K-A146T-AS | MT | MT | | | |
| B-V600E-AS | MT | MT | K-A146T-S | MT | MT | | | |
| B-V600R-AS | MT | MT | K-A146V-S | MT | MT | | | |
| B-V600K-AS | MT | MT | K-A146V-AS | MT | MT | | | |
| B-V600D-S | MT | MT | | | | | | |
| B-V600D-AS | MT | MT | | | | | | |
| B-K601E-S | MT | MT | | | | | | |

C. ERK Mutation Assay Detects Mutations in FFPE Tumor Samples

Genomic DNA was isolated from sixty FFPE samples, ten samples each of colorectal, ovarian, melanoma, lung (non-small cell carcinomas), pancreatic, and thyroid cancers. Each sample was subjected to mutation analysis by the ERK Mutation Assay (Example 12) and Sanger sequencing (Example 6). The analytical accuracy of the mutation analysis of the genomic DNA using the ERK Mutation Assay (EMA) and Sanger sequencing (Sanger) is shown in Table 8 (Colorectal: CRC; Ovarian: OVR; Thyroid: THY; Melanoma: MEL; Pancreatic: PNC; Lung: LNG). Table 9 shows the percentage of tumors with mutations in KRAS, BRAF, or NRAS as reported in the COSMIC Database (Catalogue of Somatic Mutations in Cancer, Wellcome Trust Sanger Institute, Cambridge, UK) and from the ERK Mutation Assay (EMA).

In general, Applicants found that the number and type of mutations present when analyzed with the ERK Mutation Assay was consistent with those reported in the COSMIC database (Table 9). The exceptions appear to be under reporting of BRAF and KRAS mutations in melanomas and pancreatic cancers respectively (10% and 20% versus 43%

Der, C. J., *Oncogene,* 2007, 26:3291-3310; Wistuba, I. I., et al., *Semin. Oncol.,* 2001, 28(2)(suppl 4):3-13; Davies, H., et al., *Nature,* 2002, 417:949-954; Kohno, M., and Pouyssegur, J., *Ann. Med.,* 2006, 38:200-211; Brose, M. S., et al., *Cancer Res.,* 2002, 62:6997-7000; Pratilas, C. A., and Solit, D. B., *Rev. Recent Clin. Trials,* 2007, 2:121-123). The mutation rates reported in the COSMIC database include all mutations reported for these genes, while rates reported in the literature, as well as this study, generally focus on a more restricted set of mutations. Without wishing to be bound by any theory, Applicants suggest that the small sample size used in this study may have also contributed to any discrepancy observed.

Discordant results between the EMA and Sanger results were observed in eighteen out of sixty samples. To resolve these discordant results, samples were analyzed by Ion PGM to produce a consensus result (Example 7). There was insufficient material for NGS analysis for seven (one ovarian and six melanoma cancers) of the eighteen discordant samples. The NGS results for seven of the eleven discordant samples agreed with the EMA results. The remaining four samples agreed with the Sanger sequencing results. The results for samples for which there was sufficient material with which to carry out NGS are also shown in Table 8.

TABLE 8

| Tumor Type | KRAS EMA | KRAS Sanger | KRAS NGS | NRAS EMA | NRAS Sanger | NRAS NGS | BRAF EMA | BRAF Sanger | BRAF NGS |
|---|---|---|---|---|---|---|---|---|---|
| CRC-1 | WT | WT | | Q61L | Q61L | | WT | WT | |
| CRC-2 | WT | WT | | WT | WT | | WT | WT | |
| CRC-3 | WT | WT | | WT | WT | | WT | WT | |
| CRC-4 | G13D | G13D | | WT | WT | | WT | WT | |
| CRC-5 | WT | WT | | WT | WT | | WT | WT | |
| CRC-6 | G12S | G12N | G12S | WT | WT | WT | WT | WT | WT |
| CRC-7 | G12V | G12V | | WT | WT | | WT | WT | |
| CRC-8 | WT | NC | WT | WT | WT | WT | NC | WT | WT |
| CRC-9 | WT | WT | | WT | WT | | WT | WT | |
| CRC-10 | WT | WT | | WT | WT | | V600E | V600E | |
| OVR-1 | WT | WT | | WT | WT | | WT | WT | |
| OVR-2 | WT | WT | | WT | WT | | WT | WT | |
| OVR-3 | WT | WT | | WT | WT | | WT | WT | |
| OVR-4 | WT | WT | | WT | WT | | WT | WT | |
| OVR-5** | WT | NC | ND | NC | NC | ND | WT | G466R* | ND |
| OVR-6 | WT | WT | | WT | WT | | WT | WT | |
| OVR-7 | WT | WT | | WT | WT | | WT | WT | |
| OVR-8 | WT | WT | WT | WT | WT | WT | WT | WT | WT |
| OVR-9 | WT | WT | | WT | WT | | WT | WT | |
| OVR10 | WT | WT | | WT | WT | | WT | WT | |
| THY-1 | WT | WT | | WT | WT | | V600E | V600E | |
| THY-2 | WT | WT | | WT | WT | | V600E | V600E | |
| THY-3 | WT | WT | | WT | WT | | V600E | V600E | |
| THY-4 | WT | Q61Stop* A146T | WT | WT | WT | WT | V600E | V600E | V600E |
| THY-5 | WT | WT | | WT | WT | | V600E | V600E | |
| THY-6 | WT | WT | | WT | WT | | V600E | V600E | |
| THY-7 | WT | WT | WT | WT | G13D | WT | V600E | V600E | V600E |
| THY-8 | A146T* | WT | A146T | WT | WT | WT | V600E | V600E | WT |
| THY-9 | WT | WT | | WT | WT | | V600E | V600E | |
| THY-10 | WT | WT | | WT | WT | | WT | WT | |
| MEL-1 | WT | WT | | WT | WT | | WT | WT | |
| MEL-2** | WT | NC | ND | WT | WT | ND | WT | WT | ND |
| MEL-3 | WT | WT | | Q61K | Q61K | | WT | WT | |
| MEL-4** | WT | NC | ND | WT | WT | ND | WT | WT | ND |
| MEL-5** | WT | NC | ND | WT | NC | ND | WT | NC | ND |
| MEL-6** | WT | WT | ND | WT | G13D | ND | V600E | WT | ND |
| MEL-7** | WT | NC | ND | WT | WT | ND | WT | WT | ND |
| MEL-8 | WT | WT | WT | WT | WT | WT | WT | WT | WT |
| MEL-9** | WT | NC | ND | WT | WT | ND | NC | WT | ND |
| MEL-10 | WT | WT | | WT | WT | | WT | WT | |
| PNC-1 | WT | WT | WT | WT | WT | WT | WT | NC | WT |
| PNC-2 | WT | G13D | WT | WT | WT | WT | WT | WT | WT |
| PNC-3 | G12D | G12D | | WT | WT | | WT | WT | |
| PNC-4 | G12D | NC | G12D | WT | WT | WT | WT | WT | WT |
| PNC-5 | G12D | WT | WT | WT | WT | WT | WT | NC | WT |
| PNC-6 | G12D | WT | WT | WT | WT | WT | WT | WT | WT |
| PNC-7 | G12C | NC | WT | WT | WT | WT | WT | WT | WT |
| PNC-8 | WT | WT | | WT | WT | | WT | WT | |
| PNC-9 | WT | WT | | WT | WT | | WT | WT | |
| PNC-10 | WT | WT | | WT | WT | | WT | WT | |
| LNG-1 | WT | WT | | WT | WT | | WT | WT | |
| LNG-2 | WT | NC | WT | WT | G13D | WT | WT | WT | WT |
| LNG-3 | WT | WT | | WT | WT | | WT | WT | |
| LNG-4 | WT | WT | | WT | WT | | WT | WT | |
| LNG-5 | WT | WT | | WT | WT | | WT | WT | |
| LNG-6 | WT | WT | | WT | WT | | WT | WT | |
| LNG-7 | G12D | G12D | | WT | WT | | WT | WT | |
| LNG-8 | WT | WT | | WT | WT | | WT | WT | |
| LNG-9 | WT | WT | | WT | WT | | WT | WT | |
| LNG-10 | WT | WT | | WT | WT | | WT | WT | |

*These results were only observed once and have not been reproduced.
**Insufficient material remaining for NGS analysis (ND).

TABLE 9

|  | Cosmic Database* | | | EMA* | | |
| --- | --- | --- | --- | --- | --- | --- |
|  | KRAS | BRAF | NRAS | KRAS | BRAF | NRAS |
| Colorectal | 35 | 12 | 2 | 30 | 10 | 10 |
| Melanoma | 2 | 43 | 13 | 0 | 10 | 10 |
| Ovarian | 14 | 9 | 1 | 0 | 0 | 0 |
| Pancreatic | 58 | 2 | 1 | 20 | 0 | 0 |
| Thyroid | 2 | 40 | 0 | 10 | 90 | 0 |
| Lung | 16 | 2 | 1 | 10 | 0 | 0 |

Example 14

Intra-Run Variation

A. Repeatability

To assess intra-run precision (repeatability), i.e. how well the assay performs when similar samples are assayed, eight samples from the accuracy study (Example 13) across various tumor types (colorectal, thyroid, lung, pancreatic, and ovarian), were run in replicas of eight in a single batch using the ERK Mutation Assay (Example 12). The results shown in Tables 10A and 10B were compared to the consensus call (Example 5). With the exception of one discordant result for each of the two ovarian samples and one replica of Ovarian-1 for KRAS exon 2 that failed to amplify, the repeatability was 100% for six of the eight samples for each tumor type across all three genes. Repeatability for the BRAF, KRAS and NRAS genes individually was 100% (64/64), 100% (63/63) and 97% (62/64), respectively (Table 14).

TABLE 10A

|  | Colorectal-1 | | | Colorectal-7 | | | Thyroid-2 | | | Thyroid-8 | | |
| --- | --- | --- | --- | --- | --- | --- | --- | --- | --- | --- | --- | --- |
|  | KRAS | NRAS | BRAF | KRAS | NRAS | BRAF | KRAS | NRAS | BRAF | KRAS | NRAS | BRAF |
| Truth | WT | Q61L | WT | G12V | WT | WT | WT | WT | V600E | WT | WT | V600E |
| 1 | WT | Q61L | WT | G12V | WT | WT | WT | WT | V600E | WT | WT | V600E |
| 2 | WT | Q61L | WT | G12V | WT | WT | WT | WT | V600E | WT | WT | V600E |
| 3 | WT | Q61L | WT | G12V | WT | WT | WT | WT | V600E | WT | WT | V600E |
| 4 | WT | Q61L | WT | G12V | WT | WT | WT | WT | V600E | WT | WT | V600E |
| 5 | WT | Q61L | WT | G12V | WT | WT | WT | WT | V600E | WT | WT | V600E |
| 6 | WT | Q61L | WT | G12V | WT | WT | WT | WT | V600E | WT | WT | V600E |
| 7 | WT | Q61L | WT | G12V | WT | WT | WT | WT | V600E | WT | WT | V600E |
| 8 | WT | Q61L | WT | G12V | WT | WT | WT | WT | V600E | WT | WT | V600E |

TABLE 10B

|  | Lung-7 | | | Pancreactic-3 | | | Ovarian-1 | | | Ovarian-8 | | |
| --- | --- | --- | --- | --- | --- | --- | --- | --- | --- | --- | --- | --- |
|  | KRAS | NRAS | BRAF | KRAS | NRAS | BRAF | KRAS | NRAS | BRAF | KRAS | NRAS | BRAF |
| Truth | G12D | WT | WT | G12D | WT | WT | WT | WT | WT | WT | WT | WT |
| 1 | G12D | WT | WT | G12D | WT | WT | WT | WT | WT | WT | WT | WT |
| 2 | G12D | WT | WT | G12D | WT | WT | WT | WT | WT | WT | WT | WT |
| 3 | G12D | WT | WT | G12D | WT | WT | WT | WT | WT | WT | G13D | WT |
| 4 | G12D | WT | WT | G12D | WT | WT | WT | WT | WT | WT | WT | WT |
| 5 | G12D | WT | WT | G12D | WT | WT | No Exon 2 | WT | WT | WT | WT | WT |
| 6 | G12D | WT | WT | G12D | WT | WT | WT | G12D | WT | WT | WT | WT |
| 7 | G12D | WT | WT | G12D | WT | WT | WT | WT | WT | WT | WT | WT |
| 8 | G12D | WT | WT | G12D | WT | WT | WT | WT | WT | WT | WT | WT |

B. Reproducibility

Similarly, to assess the inter-run precision (reproducibility), i.e., how well the assay performs when the samples are assayed over a period of time, eight genomic DNA samples across various tumor types (colorectal, thyroid, lung, pancreatic, and ovarian), were assayed eight times in eight batches over a period of four days. As shown in Tables 11A and 11B, with the exception of a thyroid and a colorectal sample, each having one false positive in NRAS, and a melanoma sample having two false negatives in BRAF and a false positive in KRAS, 100% reproducibility was observed for five of the eight samples. Reproducibility for the BRAF, KRAS and NRAS genes individually was 97% (62/64), 98% (61/62) and 97% (62/64), respectively (Table 12).

KRAS mutation was detected at 1.6% mutant: wild type DNA, while two other mutations were detected at 6% mutant DNA, and all mutations were detected at 12% mutant DNA.

Without wishing to be bound by any theory, Applicants believe that the results observed were affected by several factors. First, the difficulty in accurately determining the starting percentage of mutant DNA present in any given sample required an assumption that each cell line was heterozygous for the mutation. Second, the differences in extinction coefficients for the fluorescent dyes used to identify the various bases incorporated into the SNPE probes made it difficult to accurately assess the relative ratios of one nucleotide verses another. As such, a conservative estimate of the LOD was between 6 and 12% mutant DNA.

TABLE 11A

| Colorectal-1 | | | Colorectal-10 | | | Thyroid-1q | | | Thyroid-8 | | |
|---|---|---|---|---|---|---|---|---|---|---|---|
| KRAS | NRAS | BRAF | KRAS | NRAS | BRAF | KRAS | NRAS | BRAF | KRAS | NRAS | BRAF |
| WT | Q61L | WT | WT | WT | V600E | WT | WT | V600E | WT | WT | V600E |
| WT | Q61L | WT | WT | WT | V600E | WT | WT | V600E | WT | WT | V600E |
| WT | Q61L | WT | WT | WT | V600E | WT | WT | V600E | WT | WT | V600E |
| WT | Q61L | WT | WT | WT | V600E | WT | WT | V600E | WT | WT | V600E |
| WT | Q61L | WT | WT | WT | V600E | no Ex 2 | WT | V600E | WT | WT | V600E |
| WT | Q61L | WT | WT | WT | V600E | no Ex 2 | WT | V600E | WT | WT | V600E |
| WT | Q61L | WT | WT | G13D | V600E | WT | G13D | V600E | WT | WT | V600E |
| WT | Q61L | WT | WT | WT | V600E | WT | WT | V600E | WT | WT | V600E |
| WT | Q61L | WT | WT | WT | V600E | WT | WT | V600E | WT | WT | V600E |

TABLE 11B

| Ovarian-1 | | | Ovarian-8 | | | Lung-7 | | | Melanoma-6 | | |
|---|---|---|---|---|---|---|---|---|---|---|---|
| KRAS | NRAS | BRAF | KRAS | NRAS | BRAF | KRAS | NRAS | BRAF | KRAS | NRAS | BRAF |
| WT | WT | WT | WT | WT | WT | G12D | WT | WT | WT | WT | V600E |
| WT | WT | WT | WT | WT | WT | G12D | WT | WT | WT | WT | V600E |
| WT | WT | WT | WT | WT | WT | G12D | WT | WT | WT | WT | V600E |
| WT | WT | WT | WT | WT | WT | G12D | WT | WT | WT | WT | V600E |
| WT | WT | WT | WT | WT | WT | G12D | WT | WT | WT | WT | V600E |
| WT | WT | WT | WT | WT | WT | G12D | WT | WT | WT | WT | V600E |
| WT | WT | WT | WT | WT | WT | G12D | WT | WT | WT | WT | WT |
| WT | WT | WT | WT | WT | WT | G12D | WT | WT | WT | WT | WT |
| WT | WT | WT | WT | WT | WT | G12D | WT | WT | G12D | WT | V600E |

Example 15

Limit of Detection(Analytical Sensitivity)

For a qualitative assay, analytical sensitivity (limit of detection, LOD) is the lowest percentage of mutant gDNA mixed with wild type gDNA where a known mutation can be detected (CLSI guideline EP17, Protocols for Determination of Limits of Detection and Limits of Quantitation). Table 12 shows the lowest percentage of mutant DNA in a wild type background for BRAF and KRAS that can be detected in sequencing assays of the type used herein. Aliquots of gDNA from mutant cell lines (two BRAF and three KRAS) were mixed with wild type gDNA at ratios of 25%, 15%, 10%, 5%, and 1% of mutant to wild type gDNA and then analyzed by the KBN-SNPE assay. The LOD for NRAS was not performed as there were no NRAS mutant cell lines available from the American Type Culture Collection (ATCC) (Manassas, Va.). The LOD observed herein was dependent on the specific mutation or cell line used for the experiment and varied from 1.6% to 12%. For example, one

TABLE 12

| | BRAF | | KRAS | | |
|---|---|---|---|---|---|
| Cell Line | ES2 | A375 | HCT8 | Panc1 | SW527 |
| Mutation | V600E | V600E | G13D | G12D | G12V |
| % Mut DNA | | | | | |
| 25 | Yes | Yes | Yes | Yes | Yes |
| 12.5 | Yes | Yes | Yes | Yes | Yes |
| 6.25 | Yes | No | No | Yes | No |
| 3.125 | No | No | No | Yes | No |
| 1.56 | No | No | No | Yes | No |
| 0.78 | No | No | No | No | No |

Example 16

Sample Analysis in Triplicate Improves Assay Performance

In the experiments described above, Applicants noted that miscalls could occur at a rate of about 2-3%. For clinical applications, it would be desirable to appreciably reduce this error rate. Applicants hypothesized that the error rate of the assay could be reduced by assaying samples in triplicate and applying a 'majority rules' approach (Example 5). Rules for calling the results of the ERK Mutation Assay are given in Table 4.

The results for the fourteen samples, which were assayed in triplicate on three independent occasions, are shown for BRAF, KNAS, and NRAS in Tables 13A-13C, respectively (Consensus (Cnss.); Colorectal (CRC); Melanoma (MEL); Ovarian (OVR); Pancreactic (PNC); Thyroid (THY); Lung (LNG); and Concordance (Cncd.)). There were no missed calls in the BRAF and NRAS portions of the assay, while there were three indeterminate calls (one melanoma-2 and two with thyroid-1) for the KRAS portion of the assay. Under the "redo rules" for this assay, the melanoma-2 sample would have been repeated and its mutation status reported as "wild type." The thyroid-1 sample would have been repeated and its mutation status reported as "indeterminate." Thus, when samples were assayed in triplicate there was 100% (42/42) concordance between the ERK Mutation Assay result and the consensus result (defined by agreement with Sanger sequencing or NGS). Samples assayed in triplicate where two or more calls where indeterminate (ND) were excluded from calculations for concordance.

TABLE 13A

| | | BRAF | | | | | | | | |
|---|---|---|---|---|---|---|---|---|---|---|
| | | Experiment 1 | | | Experiment 2 | | | Experiment 3 | | |
| Sample | Cnss. | Rep 1 | Rep 2 | Rep 3 | Rep 1 | Rep 2 | Rep 3 | Rep 1 | Rep 2 | Rep 3 | Cncd. |
| CRC-1 | WT | WT | WT | WT | WT | WT | WT | WT | WT | WT | 3/3 |
| CRC-4 | WT | WT | WT | WT | WT | WT | WT | WT | WT | WT | 3/3 |
| CRC-7 | WT | WT | WT | WT | WT | WT | WT | WT | WT | WT | 3/3 |
| CRC-10 | V600E | V600E | V600E | V600E | V600E | V600E | V600E | V600E | V600E | V600E | 3/3 |
| MEL-2 | WT | WT | WT | WT | WT | WT | WT | WT | WT | WT | 3/3 |
| MEL-3 | WT | WT | WT | WT | WT | WT | WT | WT | WT | WT | 3/3 |
| OVR-1 | WT | WT | WT | WT | WT | WT | WT | WT | WT | WT | 3/3 |
| OVR-8 | WT | WT | WT | WT | WT | WT | WT | WT | WT | WT | 3/3 |
| PNC-3 | WT | WT | WT | WT | WT | WT | WT | WT | WT | WT | 3/3 |
| PNC-8 | WT | WT | WT | WT | WT | WT | WT | WT | WT | WT | 3/3 |
| THY-1 | V600E | V600E | V600E | V600E | V600E | V600E | V600E | V600E | V600E | V600E | 3/3 |
| THY-8 | V600E | V600E | V600E | V600E | V600E | V600E | V600E | V600E | V600E | V600E | 3/3 |
| LNG-5 | WT | WT | WT | WT | WT | WT | WT | WT | WT | WT | 3/3 |
| LNG-7 | WT | WT | WT | WT | WT | WT | WT | WT | WT | WT | 3/3 |

TABLE 13B

| | | KRAS | | | | | | | | |
|---|---|---|---|---|---|---|---|---|---|---|
| | | Experiment 1 | | | Experiment 2 | | | Experiment 3 | | |
| Sample | Cnss. | Rep 1 | Rep 2 | Rep 3 | Rep 1 | Rep 2 | Rep 3 | Rep 1 | Rep 2 | Rep 3 | Cncd. |
| CRC-1 | WT | WT | WT | WT | WT | WT | WT | ND* | WT | WT | 3/3 |
| CRC-4 | G13D | G13D | G13D | G13D | G13D | G13D | G13D | G13D | G13D | G13D | 3/3 |
| CRC-7 | G12V | G12V | G12V | G12V | G12V | G12V | G12V | G12V | G12V | G12V | 3/3 |
| CRC-10 | WT | WT | WT | WT | WT | WT | WT | WT | WT | WT | 3/3 |
| MEL-2 | WT | WT | ND* | ND | WT | WT | ND | WT | WT | ND | 2/2 |
| MEL-3 | WT | WT | WT | WT | WT | WT | WT | WT | WT | WT | 3/3 |
| OVR-1 | WT | WT | WT | WT | WT | WT | WT | WT | WT | WT | 3/3 |
| OVR-8 | WT | WT | WT | WT | WT | WT | WT | WT | G12D | WT | 3/3 |
| PNC-3 | G12D | G12D | G12D | G12D | G12D | G12D | G12D | G12D | G12D | G12D | 3/3 |
| PNC-8 | WT | WT | WT | WT | WT | WT | ND | WT | WT | ND | 3/3 |
| THY-1 | WT | ND | A146T | WT | ND | ND | WT | ND | WT | WT | 1/2 |
| THY-8 | WT | WT | WT | A146V | WT | WT | WT | WT | WT | WT | 3/3 |
| LNG-5 | WT | WT | WT | WT | WT | WT | WT | WT | WT | WT | 3/3 |
| LNG-7 | G12D | G12D | G12D | G12D | G12D | G12D | G12D | G12D | G12D | G12D | 3/3 |

*ND—No data due one or more exons missing

TABLE 13C

| | | Experiment 1 | | | Experiment 2 | | | Experiment 3 | | | |
|---|---|---|---|---|---|---|---|---|---|---|---|
| Sample | Cnss. | Rep 1 | Rep 2 | Rep 3 | Rep 1 | Rep 2 | Rep 3 | Rep 1 | Rep 2 | Rep 3 | Cncd. |
| | | | | | NRAS | | | | | | |
| CRC-1 | QA1L | Q61L | Q61L | Q61L | Q61L | Q61L | Q61L | Q61L | Q61L | Q61L | 3/3 |
| CRC-4 | WT | WT | WT | WT | WT | WT | WT | WT | WT | WT | 3/3 |
| CRC-7 | WT | WT | WT | WT | WT | WT | WT | WT | WT | WT | 3/3 |
| CRC-10 | WT | WT | WT | WT | WT | WT | WT | G12D | WT | WT | 3/3 |
| MEL-2 | WT | WT | WT | WT | WT | WT | WT | WT | WT | WT | 3/3 |
| MEL-3 | Q61K | Q61K | Q61K | Q61K | Q61K | Q61K | Q61K | Q61K | Q61K | Q61K | 3/3 |
| OVR-1 | WT | WT | WT | WT | WT | WT | WT | WT | Q61L | WT | 3/3 |
| OVR-8 | WT | WT | WT | WT | WT | WT | WT | WT | WT | WT | 3/3 |
| PNC-3 | WT | WT | WT | WT | WT | WT | WT | WT | WT | WT | 3/3 |
| PNC-8 | WT | WT | WT | WT | WT | WT | WT | WT | WT | WT | 3/3 |
| THY-1 | WT | WT | WT | WT | WT | WT | WT | G12D, G13V | WT | WT | 3/3 |
| THY-8 | WT | WT | WT | WT | WT | WT | WT | WT | WT | WT | 3/3 |
| LNG-5 | WT | WT | WT | WT | WT | WT | WT | WT | WT | WT | 3/3 |
| LNG-7 | WT | WT | WT | WT | WT | WT | WT | WT | WT | WT | 3/3 |

Example 17

Clinical Use of ERK Mutation Assay

In one embodiment of the invention, the ERK Mutation Assay is used as part of a clinical trial to identify and select patients diagnosed with cancer having an ERK Mutation for treatment with an ERK inhibitor. In this instance, patients diagnosed with cancer can be classified into two subgroups, i.e., those having one or more ERK Mutations and those lacking an ERK Mutation. How well an assay performs in a binary classification of patients is measured by its concordance (accuracy), and its sensitivity and specificity. As used herein, the sensitivity of the ERK Mutation Assay would be assessed by its ability to correctly identify samples containing a mutation listed in Table 2. Similarly, the specificity of the KBN-SNPE assay would be assessed by its ability to correctly identify samples that lack any of the KRAS, BRAF and NRAS mutations listed in Table 5. An ideal assay would be one having 100% specificity and 100% sensitivity.

Table 14 shows the performance characteristics (specificity, sensitivity, and overall concordance) for the ERK Mutation Assay at the gene level, while Table 15 shows these same performance characteristics at the sample or patient level. It should be noted that for classification of patients in a clinical setting, patient-level performance is considered to be more relevant than gene-level performance. As shown in Table 15, at the sample level the ERK Mutation assay herein had an overall concordance of 94% when samples were assayed as a single point versus 100% when assayed in triplicate. Similarly, specificity was 91%/100% for single point/triplicate assays, respectively, while sensitivity was 100% in both formats. The limit of detection varied from 2-12%, depending on the mutation (data not shown).

TABLE 14

| Samples Analyzed | Specificity/Sample-Level Negative Agreement | | | Sensitivity/Mutation-Level Positive Agreement | | | Overall Concordance (Accuracy) | | |
|---|---|---|---|---|---|---|---|---|---|
| | KRAS | NRAS | BRAF | KRAS | NRAS | BRAF | KRAS | NRAS | BRAF |
| FFPE Single Screen | 100% (44/44) | 100% (55/55) | 100% (46/46) | 70% (7/10) | 100% (2/2) | 100% (10/10) | 94% (51/54) | 100% (55/55) | 100% (51/51) |
| FFPE Triplicate Screen | 100% (27/27) | 100% (36/36) | 100% (33/33) | 100% (12/12) | 100% (6/6) | 100% (9/9) | 100% (39/39) | 100% (48/48) | 100% (42/42) |
| Intra-Run Variation | 100% (39/39) | 96% (54/56) | 100% (48/48) | 100% (24/24) | 80% (8/10) | 100% (16/16) | 100% (63/63) | 97% (62/64) | 100% (64/64) |
| Inter-Run Variation | 98% (53/54) | 96% (54/56) | 100% (32/32) | 100% (8/8) | 100% (8/8) | 94% (30/32) | 98% (61/62) | 97% (62/64) | 97% (62/64) |
| Cell line DNA | 100% (6/6) | 100% (11/11) | 100% (8/8) | 100% (5/5) | 100% (0/0) | 100% (3/3) | 100% (11/11) | 100% (11/11) | 100% (11/11) |

TABLE 15

| Samples Analyzed | Specificity/ Sample-Level Negative Agreement | Sensitivity/ Mutation-Level Positive Agreement | Overall Concordance (Accuracy) |
|---|---|---|---|
| FFPE Single Screen | 91% (32/35) | 100% (18/18) | 94% (50/53) |
| FFPE Triplicate Screen | 100% (13/13) | 100% (25/25) | 100% (38/38) |
| Intra-Run Variation | 87% (13/15) | 100% (48/48) | 97% (61/63) |
| Inter-Run Variation | 100% (16/16) | 96% (44/46) | 97% (60/62) |
| Cell line DNA | 100% (3/3) | 100% (8/8) | 100% (11/11) |

What is claimed:

1. A method for identifying an ERK Mutation in a patient diagnosed with cancer comprising:
    (a) contacting a biological sample from a patient diagnosed with cancer with all polymerase chain reaction (PCR) primers of Table 1 (SEQ ID NOs: 1-14), which target one or more ERK Mutations;
    (b) amplifying the section of said sample targeted by the PCR primers to form a PCR template containing one or more targeted ERK Mutations;
    (c) contacting the PCR template of step (b) with all single nucleotide primer extension (SNPE) probes of Table 2 (SEQ ID NO: 15-42), under hybridization conditions suitable to form one or more duplexes between the template and the SNPE probes, such that the first unpaired nucleotide base in the template immediately downstream of the 3' end of the probe in said one or more duplexes is a nucleotide base to be identified, wherein the nucleotide base to be identified is an ERK Mutation;
    (d) contacting the one or more PCR template-SNPE duplexes of step (c) with
    (i) a reaction mixture comprising a DNA polymerase; and
    (ii) a mixture of ddNTP terminators of a nucleic acid template-dependent primer extension reaction, wherein each terminator is capable of specifically terminating the extension reaction in a manner strictly dependent on the identity of the unpaired nucleotide base in the PCR template that is immediately downstream of the 3' end of the primer, wherein each terminator in the mixture is complementary to the nucleotide base to be identified, and wherein each terminator is labeled with a detectable marker;
    under conditions sufficient to carry out a template-dependent primer extension reaction to form an SNPE product, wherein said conditions permit base pairing of a complementary terminator with the nucleotide base to be identified and incorporation of the complementary terminator onto the 3' end of the primer, thereby extending said 3' end of the primer by one terminator;
    (e) determining the presence and identity of the nucleotide base to be identified at the specific position in the SNPE product by detecting the detectable marker of the incorporated terminator of step (d) while said terminator is incorporated at the 3' end of the extended primer.

2. The method of claim 1, wherein in step (d), the ddNTP terminators are a mixture of ddATP, ddCTP, ddGTP, and ddTTP.

3. The method of claim 1, wherein in step (d), the one or more duplexes from step (c) is contacted with four labeled terminators, each with a different detectable label.

4. The method of claim 1, wherein in step (e) the ERK Mutation identified is from the group consisting of the mutations of Table 5.

5. A method for identifying a patient previously diagnosed with cancer as a patient who should undergo treatment with an ERK inhibitor comprising:
    (a) contacting a biological sample from a patient diagnosed with cancer with all of polymerase chain reaction (PCR) primers of Table 1 (SEQ ID NOs: 1-14), which target one or more ERK Mutations;
    (b) amplifying the section of said sample targeted by the PCR primers to form a PCR template containing one or more targeted ERK Mutations;
    (c) contacting the PCR template of step (b) with all of single nucleotide primer extension (SNPE) probes, of Table 2 (SEQ ID NO: 15-42), under hybridization conditions suitable to form one or more duplexes between the template and the SNPE probes, such that the first unpaired nucleotide base in the template immediately downstream of the 3' end of a probe in said one or more duplexes is a nucleotide base to be identified, wherein the nucleotide base to be identified is an ERK Mutation;
    (d) contacting the one or more PCR template-SNPE duplexes of step (c) with
    (i) a reaction mixture comprising a DNA polymerase; and
    (ii) a mixture of ddNTP terminators of a nucleic acid template-dependent primer extension reaction, wherein each terminator is capable of specifically terminating the extension reaction in a manner strictly dependent on the identity of the unpaired nucleotide base in the PCR template that is immediately downstream of the 3' end of the primer, wherein each terminator in the mixture is complementary to the nucleotide base to be identified, and wherein each terminator is labeled with a detectable marker;
    under conditions sufficient to carry out a template-dependent primer extension reaction to form an SNPE product, wherein said conditions permit base pairing of a complementary terminator with the nucleotide base to be identified and incorporation of the complementary terminator onto the 3' end of the primer, thereby extending said 3' end of the primer by one terminator;
    (e) determining the presence and identity of the nucleotide base to be identified at the specific position in the SNPE product by detecting the detectable marker of the incorporated terminator of step (d) while said terminator is incorporated at the 3' end of the extended primer; and
    wherein the patient is identified as having an ERK Mutation as determined by the identified nucleotide base at the specific position in the SNPE product.

6. The method according to claim 5, further comprising the step of treating the identified patient with an ERK inhibitor.

7. The method of claim 5, wherein in step (d), the ddNTP terminators are a mixture of ddATP, ddCTP, ddGTP, and ddTTP.

8. The method of claim 5, wherein in step (d), the one or more duplexes from step (c) is contacted with four labeled terminators, each with a different detectable label.

9. The method of claim 5, wherein in step (e) the ERK Mutation identified is from the group consisting of the mutations of Table 5.

10. A method for treating a patient diagnosed with an ERK associated cancer with an ERK inhibitor comprising:
    (a) contacting a biological sample from a patient diagnosed with cancer with all polymerase chain reaction (PCR) primers of Table 1 (SEQ ID NOs: 1-14), which target one or more ERK Mutations;
    (b) amplifying the section of said sample targeted by the PCR primers to form a PCR template containing one or more targeted ERK Mutations;
    (c) contacting the PCR template of step (b) with all of single nucleotide primer extension (SNPE) probes of Table 2 (SEQ ID NO: 15-42), under hybridization conditions suitable to form one or more duplexes between the template and the SNPE probes, such that the first unpaired nucleotide base in the template immediately downstream of the 3' end of a probe in said one or more duplexes is a nucleotide base to be identified, wherein the nucleotide base to be identified is an ERK Mutation;

(d) contacting the one or more PCR template-SNPE duplexes of step (c) with (i) a reaction mixture comprising a DNA polymerase; and
(ii) a mixture of ddNTP terminators of a nucleic acid template-dependent primer extension reaction, wherein each terminator is capable of specifically terminating the extension reaction in a manner strictly dependent on the identity of the unpaired nucleotide base in the PCR template that is immediately downstream of the 3' end of the primer, wherein each terminator in the mixture is complementary to the nucleotide base to be identified, and wherein each terminator is labeled with a detectable marker;

under conditions sufficient to carry out a template-dependent primer extension reaction to form an SNPE product, wherein said conditions permit base pairing of a complementary terminator with the nucleotide base to be identified and incorporation of the complementary terminator onto the 3' end of the primer, thereby extending said 3' end of the primer by one terminator;

(e) determining the presence and identity of the nucleotide base to be identified at the specific position in the SNPE product by detecting the detectable marker of the incorporated terminator of step (d) while said terminator is incorporated at the 3' end of the extended primer; and (f) determining the presence and identity of an ERK Mutation from the identified nucleotide base at the specific position in the SNPE product; and (g) treating the patient identified as having an ERK Mutation with an ERK inhibitor.

11. The method of claim 10, wherein in step (d), the ddNTP terminators are a mixture of ddATP, ddCTP, ddGTP, and ddTTP.

12. The method of claim 10, wherein in step (d), the one or more duplexes from step (c) is contacted with four labeled terminators, each with a different detectable label.

13. The method of claim 10, wherein in step (f) the ERK Mutation identified is from the group consisting of the mutations of Table 5.

14. The method of claim 10, wherein the cancer is selected from the group consisting of melanoma, pancreatic cancer, thyroid cancer, colorectal cancer, lung cancer, breast cancer, and ovarian cancer.

15. A kit for the detection of an ERK Mutation in a patient diagnosed with cancer comprising the PCR primers of Table 1 (SEQ ID NOs: 1-14) and the SNPE probes of Table 2(SEQ ID NOs: 15-42).

* * * * *